(12) United States Patent
Healy et al.

(10) Patent No.: US 9,339,446 B2
(45) Date of Patent: May 17, 2016

(54) GEL COMPOSITION

(75) Inventors: Lin Lu Healy, Houston, TX (US); Jack C. Cunningham, Jr., Houston, TX (US); David S. Morrison, The Woodlands, TX (US); Wei Song, Houston, TX (US); Gina Butuc, Houston, TX (US)

(73) Assignee: Calumet Penreco, LLC, Indianapolis, IN (US)

( * ) Notice: Subject to any disclaimer, the term of this patent is extended or adjusted under 35 U.S.C. 154(b) by 0 days.

(21) Appl. No.: 12/801,535

(22) Filed: Jun. 14, 2010

(65) Prior Publication Data

US 2011/0045983 A1    Feb. 24, 2011

Related U.S. Application Data

(63) Continuation of application No. 12/319,751, filed on Jan. 12, 2009, now abandoned, which is a continuation of application No. 10/665,943, filed on Sep. 19, 2003, now abandoned, which is a continuation of application No. 09/419,571, filed on Oct. 18, 1999, now abandoned.

(60) Provisional application No. 60/106,094, filed on Oct. 29, 1998.

(51) Int. Cl.

| *C08K 5/10* | (2006.01) |
|---|---|
| *A61K 8/04* | (2006.01) |
| *A61K 8/37* | (2006.01) |
| *A61K 8/90* | (2006.01) |
| *A61Q 1/00* | (2006.01) |
| *A61Q 15/00* | (2006.01) |
| *A61Q 19/00* | (2006.01) |
| *A61Q 19/04* | (2006.01) |

(52) U.S. Cl.
CPC . *A61K 8/042* (2013.01); *A61K 8/37* (2013.01); *A61K 8/90* (2013.01); *A61Q 1/00* (2013.01); *A61Q 15/00* (2013.01); *A61Q 19/00* (2013.01); *A61Q 19/04* (2013.01); *C08K 5/10* (2013.01)

(58) Field of Classification Search
CPC ........... A61K 8/042; A61K 8/37; A61K 8/90; C08K 5/10–5/12
USPC .................................. 524/311, 312, 313, 292
See application file for complete search history.

(56) References Cited

U.S. PATENT DOCUMENTS

| 3,645,705 A | 2/1972 | Miller et al. |
| 3,819,342 A | 6/1974 | Gunderman et al. |
| 4,231,369 A | 11/1980 | Sorensent et al. |

(Continued)

FOREIGN PATENT DOCUMENTS

| EP | 0147146 A2 | 7/1985 |
| EP | 0210655 A2 | 2/1987 |

(Continued)

OTHER PUBLICATIONS

International Search Report for related PCT International Application No. PCT/US99/24840 dated Feb. 24, 2000 (2 pages).

(Continued)

*Primary Examiner* — Peter D Mulcahy
(74) *Attorney, Agent, or Firm* — Barnes & Thornburg LLP

(57) ABSTRACT

A gel, comprising: an ester and a polymer having at least one of the following rigid block groups; polystyrene, polyethylene, polyvinyl chloride, and phenolics as well as one elastic block that is a member of the group consisting of ethylene/butadiene copolymers, polyisoprene, polybutadiene, ethylene/propylene copolymers, or ethylene-propylene/diene copolymers, wherein the polymer is either triblock copolymers, star polymers, radial polymers, multi-block copolymers, or combinations thereof, wherein the composition is substantially free of mineral oils; wherein the ester's chemical formula is:

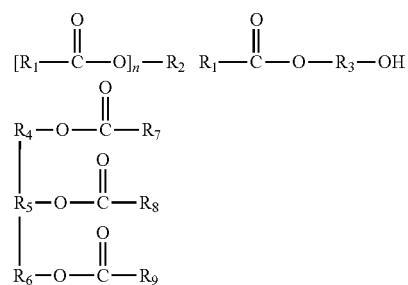

Wherein n=1, 2, 3, and 4, and $R_1$ represents a member of the group consisting of: hydrogen, hydrocarbyl, phenyl, methoxyphenyl, alkylphenyl, substituted alkyl, and substituted phenyl; $R_2$ represents a member of the group consisting of: hydrogen, hydrocarbyl, phenyl, methoxyphenyl, alkylphenyl, substituted alkyl, substituted phenyl, alkylene, phenylene, substituted alkylene, and substituted phenylene, and $R_3$ represents a member of the group consisting of: alkylene, phenylene, substituted alkylene, or substituted phenylene, and wherein $R_4$, $R_5$, $R_6$ all represent a member of the group consisting of: alkylene, phenylene, substituted alkylene, or substituted phenylene, and $R_7$, $R_8$, $R_9$ all represent a member of the group consisting of: hydrogen, hydrocarbyl, phenyl, methoxyphenyl, alkylphenyl, substituted alkyl, and substituted phenyl.

14 Claims, 4 Drawing Sheets

(56) References Cited

U.S. PATENT DOCUMENTS

| | | | |
|---|---|---|---|
| 4,427,812 | A | 1/1984 | Peiffer et al. |
| 4,540,510 | A | 9/1985 | Karl |
| 4,748,199 | A | 5/1988 | Takiguchi et al. |
| 5,132,355 | A | 7/1992 | Nahlovsky |
| 5,221,534 | A | 6/1993 | DesLauriers et al. |
| 5,399,627 | A | 3/1995 | Diehl et al. |
| 5,412,022 | A | 5/1995 | Andres et al. |
| 5,456,745 | A | 10/1995 | Roreger et al. |
| 5,508,334 | A | 4/1996 | Chen |
| 5,558,872 | A | 9/1996 | Jones et al. |
| 5,578,089 | A | 11/1996 | Elsamaloty |
| 5,635,171 | A | 6/1997 | Nadaud |
| 5,688,855 | A | 11/1997 | Stoy et al. |
| 5,756,082 | A | 5/1998 | Cashin et al. |
| 5,843,194 | A | 12/1998 | Spaulding |
| 5,879,694 | A | 3/1999 | Morrison et al. |
| 6,111,055 | A * | 8/2000 | Berger et al. ............ 528/310 |
| 6,156,713 | A | 12/2000 | Chopra et al. |
| 6,352,963 | B2 | 3/2002 | Ramin et al. |
| 6,433,068 | B1 | 8/2002 | Morrison et al. |

FOREIGN PATENT DOCUMENTS

| | | |
|---|---|---|
| EP | 0497144 B1 | 9/1995 |
| EP | 0898958 A1 | 3/1999 |
| EP | 0898960 A1 | 3/1999 |
| WO | WO 9105014 A * | 4/1991 |
| WO | 98/17243 A1 | 4/1998 |
| WO | 98/42298 A1 | 10/1998 |
| WO | 99/27042 A1 | 6/1999 |

OTHER PUBLICATIONS

English Translation of Notice of Reasons for Rejection for Japanese Patent Application No. 2009-279889, mailing date Oct. 16, 2012 (3 sheets).

Partial English Translation of Japanese Unexamined Patent Publication (Kokai) No. 03-247699, publication date (Kokai) Nov. 5, 1991 (2 sheets).

Partial English Translation of Japanese Unexamined Patent Publication (Kokai) No. 02-88644, publication date (Kokai) May 28, 1990 (1 sheet).

* cited by examiner

Diblock Copolymer

Triblock Copolymer

Radial Copolymer

Star Copolymer

Multi-Block Copolymer

Multi-Block Copolymer

GEL COMPOSITION

CROSS-REFERENCE TO RELATED APPLICATIONS

This application is a continuation application of U.S. patent application Ser. No. 12/319,751 filed on Jan. 12, 2009 now abandoned, which is a continuation of U.S. patent application Ser. No. 10/665,943 filed on Sep. 19, 2003 now abandoned, which is a continuation of U.S. patent application Ser. No. 09/419,571, filed on Oct. 18, 1999 now abandoned, which claims benefit of U.S. Provisional Patent Application No. 60/106,094, filed Oct. 29, 1998, the disclosures of which are incorporated herein in their entirety.

FIELD OF THE INVENTION

This invention relates to gel compositions which include esters, ethers, alcohols, naturally-occurring fats and oils, or mixtures thereof.

BACKGROUND OF THE INVENTION

Numerous gel compositions are known in the art. Some have proven to be a convenient and efficient vehicle or carrier for the application of various active ingredients to the skin. Such active ingredients include antiperspirants, deodorants, perfumes, sunscreens, cosmetics, emollients, insect repellants, medicaments, and the like. Products incorporating a gel composition and those made entirely from a gel composition may be in the form of a soft gel or a stick. Rubbing a soft gel or solid stick containing an effective amount of an active ingredient dissolved or dispersed therein against the skin causes transfer of the gel composition to the skin surface in a layer form, leaving the active ingredient within the layer on the desired skin surface.

For topical administration of various cosmetic and health and beauty materials to the skin, a gel composition preferably should have one or more of the following desired properties: transparency, compatibility with the active ingredient, controlled release of the active ingredient, minimization of skin irritation, and the ability to suspend organic and inorganic materials, such as color pigments, glitters, water, air, metal oxides, sunscreen active particulates, and fragrances. In sunscreen applications, it is desirable if the gel itself could act as a sunscreen active ingredient. Moreover, it should moisturize the skin and exhibit water wash-off resistance, but should not have significant syneresis. For industrial applications, a gel base may offer one or more of the following properties: suspension, moisture barrier, rheology, solvency, controlled release, wetting, self-emulsifying, etc. For example, in the paint industry the properties that are important are suspension and controlled release.

A gel composition typically is made by mixing one or more compounds to be gelled with a gelling agent. Known gelling agents include metal soaps, surfactants, homopolymers, ionic homopolymers and copolymers, fumed silica, natural derivatives of gums, waxes, clay, and so on. Common gelling agents for cosmetic oils are fatty acid soaps of lithium, calcium, sodium, aluminum, zinc, and barium. A number of homopolymers and copolymers, such as atatic ethylene-propylene copolymers, have been used to gel hydrocarbons. For example, gelled mineral oils have been available; however, gel compositions including an ester, ether, alcohol, or vegetable oil are less common. Because gel compositions including an ester, alcohol, ether, or naturally-occurring fat or oil may provide a better alternative to hydrocarbon gels, there is a need for exploring methods of making such gel compositions.

SUMMARY OF THE INVENTION

The invention meets the aforementioned need in one or more of the following aspects. In one aspect, the invention relates to a gel composition that includes an ester compound and a polymer compound selected from the group consisting of triblock copolymers, star polymers, radial polymers, multi-block copolymers, and combinations thereof. The gel composition optionally may include a diblock copolymer. When the gel composition includes a diblock copolymer, the gel composition preferably is substantially free of mineral oils. In some embodiments, the gel composition may further include a suspended component. In other embodiments, the gel composition may further include an active ingredient. The active ingredient includes, but is not limited to, sun screens, antiperspirants, deodorants, perfumes, cosmetics, emollients, insect repellants, pesticides, herbicides, fungicides, plasticizers, insecticides, and medicaments.

In another aspect, the invention relates to a gel composition which includes at least two components. The first component is a compound selected from the group consisting of alcohols, ethers, naturally-occurring fats and oils, and combinations thereof. The second component is a polymer compound selected from the group consisting of diblock copolymers, triblock copolymers, star polymers, radial polymers, multi-block copolymers, and combinations thereof. In some embodiments, suitable alcohols include, but are not limited to, octyl dodecanol and isostearyl alcohol. In other embodiments, suitable ethers include, but are not limited to, dicarylyl ether. In still other embodiments, suitable naturally-occurring fats and oils include, but are not limited to, linseed oil, soybean oil, sunflower seed oil, corn oil, sesame oil, olive oil, castor oil, coconut oil, palm oil, and peanut oil.

In yet another aspect, the invention relates to a gel composition which includes at least two components. The first component is a compound selected from the group consisting of esters, alcohols, ethers, naturally-occurring fats and oils, and combinations thereof. The second component is a polymer compound selected from the group consisting of alkyl galactomannan, polybutadiene, and combinations thereof.

In still another aspect, the invention relates to a method of making a gel composition. The method includes (a) mixing an ester compound with a polymer compound selected from the group consisting of triblock copolymers, star polymers, radial polymers, multi-block copolymers, and combinations thereof; (b) heating the mixture; (c) agitating the mixture until the mixture becomes homogeneous; and (d) cooling the mixture.

In still yet another aspect, the invention relates to a method of making a gel composition. The method includes (a) mixing an alcohol, an ether, or a naturally-occurring fat or oil with a polymer compound selected from the group consisting of diblock copolymers, triblock copolymers, star copolymers, radial polymers, multi-block copolymers, and combinations thereof, (b) heating the mixture; (c) agitating the mixture until the mixture becomes homogeneous; and (d) cooling the mixture.

In another aspect, the invention relates to a method of making a gel composition. The method includes (a) mixing an ester, an alcohol, an ether, or a naturally-occurring fat or oil with alkyl galactomannan, or polybutadiene; (b) heating the mixture; (c) agitating the mixture until the mixture becomes homogeneous; and (d) cooling the mixture.

Properties and advantages of the embodiments of the invention become apparent with the following description.

DESCRIPTION OF EMBODIMENTS OF THE INVENTION

Figure 1:
FIG. 1 is a schematic illustrating the chain structure of a diblock copolymer used in embodiments of the invention.

Embodiments of the invention are, in part, based on the discovery that esters, alcohols, ethers, and naturally-occurring fats and oils can be gelled by using selected polymeric gelling agents. For example, diblock copolymers, triblock copolymers, radial polymers, star polymers, multi-block copolymers, butyl rubbers, alkyl galactomannan, and mixtures thereof can be used as gelling agents to obtain gelled esters, gelled ethers, gelled alcohols, and gelled naturally-occurring fats and oils. In some embodiments, the gel compositions and products made therefrom are transparent or substantially transparent. In other embodiments, the gel compositions and products made therefrom are semi-transparent, hazy, or opaque. These gel compositions and products made therefrom each have numerous cosmetic and industrial applications.

A gel refers to a two-phase colloidal system comprising a liquid and a solid in the form of thickened liquid, semi-solid or solid. A gel also can refer to a composition that is either physically cross-linked by virtue of entangled polymer chains, or chemically cross-linked by virtue of covalent bonds such that it swells, but does not dissolve, in the presence of liquid. A gel typically is obtained by use of a gelling agent. The term "polymer" used herein includes both homopolymer and copolymer. A homopolymer is a polymer obtained by polymerizing one type of monomer, whereas a copolymer is a polymer obtained by polymerizing two or more types of monomers. "Block copolymer" refers to a copolymer in which like monomer units occur in relatively long, alternate sequences on a chain.

The term "opaque" refers to the optical state of a medium whose molecular aggregation is such that light cannot pass through. Therefore, light transmission through an opaque medium is substantially close to zero. On the other hand, the term "transparent" refers to the optical state of a medium through which light can pass through so that an object can be seen through it. As defined, the term "transparent" includes any optical state which is not opaque. A medium is considered transparent even if only a small fraction of light passes through it. Thus, a clear gel and a translucent gel are considered transparent.

In some embodiments of the invention, a block copolymer capable of forming a three-dimensional network through physical cross-linking is used as the gelling agent. Suitable block copolymers include at least one rigid block and one elastomeric block. The rigid blocks of a block copolymer form rigid domains through which physical cross-linking may occur. The physical cross-linking via these rigid domains yields a continuous three-dimensional network. In the presence of heat, shear, or solvent, the rigid domains soften and permit flow. Upon cooling, removal of shear, or solvent evaporation, the rigid domains reform and harden, locking the elastomeric network in place. Preferably, suitable block copolymers include diblock copolymers, triblock copolymers, radial polymers, star polymers, multi-block copolymers, and mixtures thereof.

The amount of a gelling agent may range from about 0.2% to about 80% by weight, depending on the desired properties of the resulting gel. Preferably, a gelling agent is present in the gel from about 1% to about 40% by weight. More preferably, a gelling agent is present in the gel about 5% to about 20% by weight. In embodiments where both a diblock copolymer and a triblock copolymer are used, the triblock copolymer may range from about 0.1% to about 10%, and the diblock copolymer from about 1% to about 40%.

FIG. 1 illustrates the typical chain structure of a diblock copolymer. The polymer chain of the diblock copolymer includes two blocks: a rigid block and an elastomeric block. The rigid block is represented by diamonds. The elastomeric block is represented by circles. The rigid block typically is composed of polystyrene, polyethylene, polyvinylchloride, phenolics, and the like; the elastomeric block may be composed of, ethylene/butadiene copolymers, polyisoprene, polybutadiene, ethylene/propylene copolymers, ethylene-propylene/diene copolymers, and the like. As such, suitable diblock copolymers include, but are not limited to, styrene-ethylene/propylene copolymers, styrene-ethylene/butadiene copolymers, styrene-isoprene copolymers, styrene-butadiene copolymers.

Figure 2:
FIG. 2 is a schematic illustrating the chain structure of a triblock copolymer used in embodiments of the invention.
Figure 5A:
FIGS. 5A-5B are schematics illustrating the chain structure of multi-block copolymers used in embodiments of the invention.
Figure 5B:

FIG. 2 illustrates the chain structure of a triblock copolymer. As illustrated in FIG. 2, each polymer chain includes two rigid blocks at either end and a middle block which is elastomeric. This is a preferred triblock copolymer structure, although a triblock copolymer with two elastomeric end blocks and a rigid middle block also can be used. Suitable triblock copolymers include, but are not limited to, styrene-ethylene/propylene-styrene copolymers, styrene-ethylene/butadiene-styrene copolymers, styrene-isoprene-styrene copolymers, and styrene-butadiene-styrene copolymers. Multi-block copolymers are similar to diblock copolymers or triblock copolymers, except that the multiple block copolymers include additional elastomeric blocks and/or rigid blocks as illustrated in FIGS. 5A-5B.

Figure 3:
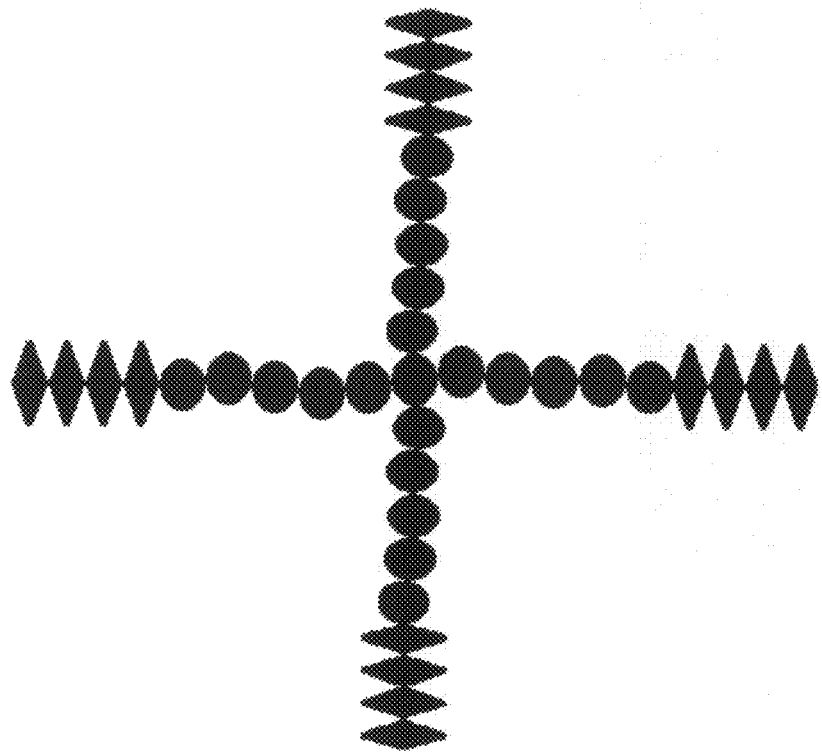
FIG. 3 is a schematic illustrating the chain structure of a radial polymer used in embodiments of the invention.
Figure 4:
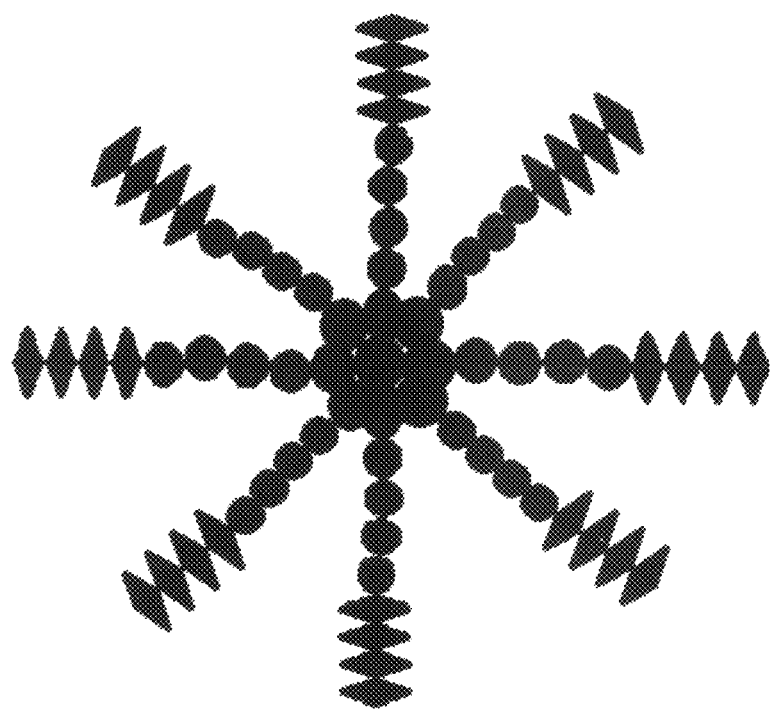
FIG. 4 is a schematic illustrating the chain structure of a star polymer used in embodiments of the invention.

In addition to the linear chain structure, branched homopolymers or copolymers also may be used. FIGS. 3-4 illustrate the chain structure of a radial polymer and a star polymer. It should be noted that one or more functional groups may be grafted onto the chain of any of the aforementioned polymers. In other words, any of the above polymers may be modified by grafting. Suitable functional groups for grafting depend on the desired properties. For example, one or more ester groups, silane groups, silicon-containing groups, maleic anhydride groups, acrylamide groups, and acid groups may be grafted. In addition to grafting, the above polymers may be hydrogenated to reduce unsaturation before they are used as gelling agents.

Numerous commercially available block copolymers may be used in embodiments of the invention. For example, various grades of copolymers sold under the trade name of Kraton.® from Shell Chemical Company can be used as a gelling agent. In addition, copolymers sold under the trade name of Vector.®. available from Dexco® and Septon.®. from Kuraray also may be used. U.S. Pat. No. 5,221,534, U.S. Pat. No. 5,578,089, and U.S. Pat. No. 5,879,694 disclose block copolymers which may be used in embodiments of the invention, the disclosures of the three patents are incorporated by reference in their entirety herein. Table 1 lists some commercially available block copolymers which may be used in embodiments of the invention. It is noted that additional suitable block copolymers may include, but are not limited to, polystyrene/polyester, polyether/polyamide, polyether/polyester, polyester/polyamide, polyether/polyurethane, polyester/polyurethane, poly(ethylene oxide)/poly(propylene oxide), nylon/rubber, and polysiloxane/polycarbonate.

TABLE 1

| Copolymer | Block Type | Polystyrene Content (%) | Comment |
|---|---|---|---|
| Kraton ® G 1702 | SEP | 28 | hydrogenated diblock |
| Kraton ® G 1701 | SEP | 37 | hydrogenated diblock |
| Kraton ® G 1780 | SEP | 7 | Star polymer |
| Kraton ® G 1650 | SEBS | 30 | hydrogenated triblock |
| Kraton ® G 1652 | SEBS | 30 | hydrogenated triblock |
| Kraton ® D 1101 | SEBS + SEP | 31 | triblock and diblock mixture (85:15) |
| Kraton ® D 1102 | SEBS + SEP | 28 | triblock + diblock (85:15) |
| Kraton ® D 1133 | SEBS + SEP | 35 | triblock + diblock (66:34) |
| Kraton ® FG 1901 | SEBS | 30 | triblock (hydrogenated and functionally grafted with 1.7% of maleic anhydride |
| Septon ® 1001 | SEP | 35 | hydrogenated diblock |
| Vector ® 6030 | SEP | 30 | Unsaturated diblock |
| Vector ® 8550 | SBS | 29 | Unsaturated triblock |
| Vector ® 2518P | SBS | 31 | Unsaturated triblock |
| Solprene ® 1430 | SB | 40 | Unsaturated diblock |

Note:
SEP denotes to Styrene/ethylene/propylene copolymers
SEBS denotes to styrene/ethylene/bytulene/styrene copolymers
SB denotes to styrene/butadiene copolymers
SBS denotes to styrene-butadiene-styrene copolymers It should be noted that block copolymers are not the only gelling agents that can be used in embodiments of the invention. Other types of polymers also may be used. Homopolymers which are capable of effecting strong molecular interaction between polymeric chains can be used as gelling agents. One such example is butyl rubber, which can thicken oil due to its compatibility with oil and high molecular weight. Specifically, a polybutadiene polymer sold under the trademark of Solprene®. S200, which is available from GIRSA Industrias Negromex, S.A.de C.V. (INSA), can be used as a gelling agent. Other homopolymers capable of forming hydrogen bonding may include polyamide, polyester, and polyolefin. Still another example is alkyl galactomannan, which is capable of forming strong hydrogen bonding. Alkyl galactomannan is available from Hercules Incorporated under the trade name of N-HANCE AG50 and AG200. Alkyl galactomannan is a polymer obtained by modifying natural products. It is especially effective in gelling esters and naturally-occurring fats and oils.

In accordance with embodiments of the invention, a gelled ester composition is obtained by gelling an ester compound with a triblock copolymer, a star polymer, a radial polymer, a multi-block copolymer, or mixtures thereof. Optionally, the gelled ester composition may further include one or more diblock copolymers. When a diblock copolymer is used along with one of triblock copolymers, star polymers, radial polymers, and multi-block copolymers, the resulting gel composition is substantially free of mineral oils. Suitable esters also may be gelled by alkyl galactomannan, polybutadiene, or other aforementioned polymers.

Any ester compound may be used in embodiments of the invention to obtain a gelled ester composition. An ester is defined as a compound that includes one or more carboxylate groups: R—COO—, where R is hydrogen, hydrocarbyl, phenyl, methoxyphenyl, alkylphenyl, substituted alkyl, substituted phenyl, or other organic radicals. Suitable esters include monoesters, diesters, triesters, etc. For example, one class of suitable esters that can be gelled is represented by the following formulas:

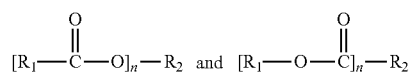

where n=1, 2, 3, and 4, and $R_1$ includes hydrogen, hydrocarbyl, phenyl, methoxyphenyl, alkylphenyl, substituted alkyl, and substituted phenyl; and $R_2$ includes hydrogen, hydrocarbyl, phenyl, methoxyphenyl, alkylphenyl, substituted alkyl, substituted phenyl, alkylene, phenylene, substituted alkylene, substituted phenylene, etc. It is noted that a suitable group for $R_2$ depends on whether n is 1, 2, 3, or 4.

Another class of suitable esters that may be gelled in embodiments of the invention is represented by the following formula:

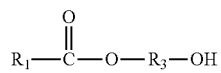

where $R_3$ includes alkylene, phenylene, substituted alkylene, and substituted phenylene.

Still another class of suitable esters that may be gelled in embodiments of the invention is represented by the following formula:

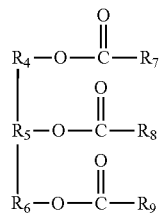

where $R_4$, $R_5$, and $R_6$ individually include alkylene, phenylene, substituted alkylene, and substituted phenylene; $R_7$, $R_8$, and $R_9$ individually include hydrogen, hydrocarbyl, phenyl, methoxyphenyl, alkylphenyl, substituted alkyl, and substituted phenyl.

Preferred esters and their chemical formulas are listed in Table 2.

TABLE 2

| Chemical Name | Chemical Formula |
|---|---|
| Isononyl Isononanoate | $C_8H_{17}\text{—}\underset{\underset{O}{\parallel}}{C}\text{—O—}C_9H_{19}$ |
| Isopropyl Palmitate | $C_{15}H_{31}\text{—}\underset{\underset{O}{\parallel}}{C}\text{—O—}C_3H_7$ |
| $C_{12\text{-}15}$ alkyl benzoate | Ph-$\underset{\underset{O}{\parallel}}{C}$—O—$C_{12\text{-}15}$ |
| Myristyl Neopentanoate | $C_7H_{15}\text{—}\underset{\underset{O}{\parallel}}{C}\text{—O—}[CH_2]_{13}\text{—}CH_3$ |
| Tridecyl Salicylate | 2-hydroxybenzoate—O—$C_{13}H_{27}$ |
| Ocytyl Methoxycinnamate | $CH_3\text{—O—}Ph\text{—}\underset{H}{\overset{H}{C}}=\underset{H}{\overset{}{C}}\text{—}\underset{\underset{O}{\parallel}}{C}\text{—}CH_2\text{—}C_7H_{13}$ |
| Propylene glycol dicaprylate/caprate | $CH_3\text{—}[CH_2]_6\text{—}\underset{\underset{O}{\parallel}}{C}\text{—O—}CH_2\text{—}\underset{CH_3}{\overset{}{CH}}\text{—O—}\underset{\underset{O}{\parallel}}{C}\text{—}[CH_2]_6\text{—}CH_3$ |
| Pentaerythrityl tetraisostearate | (tetraester of pentaerythritol, R represents fatty acid radicals derived from coconut oil) |
| Trimethylolpropane triisostearate | (triester of trimethylolpropane, R represents fatty acid radicals derived from coconut oil) |
| Glyceryl isostearate | $C_{17}H_{35}\text{—}\underset{\underset{O}{\parallel}}{C}\text{—O—}CH_2\text{—}\underset{OH}{\overset{}{CH}}\text{—}CH_2OH$ |
| Diisononyl adipate | $C_9H_{19}\text{—O—}\underset{\underset{O}{\parallel}}{C}\text{—}[CH_2]_4\text{—}\underset{\underset{O}{\parallel}}{C}\text{—O—}C_9H_{19}$ |

TABLE 2-continued

| Chemical Name | Chemical Formula |
|---|---|
| Trioctyldodecyl citrate | $$\begin{array}{c} \text{CH}_2-\overset{\overset{\displaystyle O}{\|}}{C}-O-R \\ | \\ \text{HO}-\overset{|}{C}-\overset{\overset{\displaystyle O}{\|}}{C}-O-R \\ | \\ \text{CH}_2-\overset{\overset{\displaystyle O}{\|}}{C}-O-R \end{array}$$ (R is a octyl dodecyl) |

Other suitable esters include, but are not limited to, the following compounds: Acefylline Methylsilanol Mannuronate; Acetaminosalol; Acetylated Cetyl Hydroxyprolinate; Acetylated Glycol Stearate; Acetylated Sucrose Distearate; Acetylmethionyl Methylsilanol Elastinate; Acetyl Tributyl Citrate; Acetyl Triethyl Citrate; Acetyl Trihexyl Citrate; Aleurites Moluccana Ethyl Ester; Allethrins; Allyl Caproate; Amyl Acetate; Amyl Benzoate; Amyl Salicylate; Arachidyl Behenate; Arachldyl Glycol Isostearate; Arachldyl Propionate; Ascorbyl Dipalmitate; Ascorbyl Palmitate; Ascorbyl Stearate; Aspartame; Batyl Isostearate; Batyl Stearate; Bean Palmitate; Behenyl Beeswax; Behenyl Behenate; Behenyl Benzoate; Behenyl Erucate; Behenyl Isostearate; Behenyl/Isostearyl Beeswax; 1,2,4-Benzenetriacetate; Benzoin (Styrax Bensoin) Gum; Benzoxiquine; Benzyl Acetate; Benzyl Benzoate; Benzyl Cinnamate; Benzyl Hyaluronate; Benzyl Laurate; Benzyl Nicotinate; Benzylparaben; Benzyl Salicylate; Beta-Sitosteryl Acetate; Borago Officinalis Ethyl Ester; Butoxyethyl Acetate; Butoxyethyl Nicotinate; Butoxyethyl Stearate; Butyl Acetate; Butyl Acetyl Ricinoleate; Butyl Benzoate; Butyl Benzyl Phthalate; 2-t-Butylcyclohexyl Acetate; Butylene Glycol Dicaprylate/Dicaprate; Butylene Glycol Montanate; Butyl Ester of Ethylene/MA Copolymer; Butyl Ester of PVM/MA Copolymer; Butylglucoside Caprate; Butyl Isostearate; Butyl Lactate; Butyl Methacrylate; Butyl Myristate; Butyloctyl Beeswax; Butyloctyl Benzoate; Butyloctyl Candelillate; Butyloctyl Oleate; Butyloctyl Salicylate; Butyl Oleate; Butyl PABA; Butylparaben; Butyl Phthalyl Butyl Glycolate; Butyl Stearate; Butyl Thioglycolate; Butyroyl Trihexyl Citrate; C18-36 Acid Glycol Ester; C12-20 Acid PEG-8 Ester; Caffeine Benzoate; Calcium Pantetheine Sulfonate; Calcium Stearoyl Lactylate; C-18-28 Alkyl Acetate; C18-38 Alkyl Beeswax; C30-50 Alkyl Beeswax; C20-40 Alkyl Behenate; C18-38 Alkyl C24-54 Acid Ester; C-8 Alkyl Ethyl Phosphate; C18-38 Alkyl Hydroxystearoyl Stearate; C12-13 Alkyl Lactate; C12-15 Alkyl Lactate; C12-13 Alkyl Octanoate; C12-15 Alkyl Octanoate; C12-15 Alkyl Salicylate; C18-36 Alkyl Stearate; C20-40 Alkyl Stearate; C30-50 Alkyl Stearate; C40-60 Alkyl Stearate; Caproyl Ethyl Glucoside; Caployl Salicylic Acid; Caprylyl Butyrate; Castor Oil Benzoate; C10-30 Cholesterol/Lanosterol Esters; Cellulose Acetate; Cellulose Acetate Butyrate; Cellulose Acetate Propionate; Cellulose Acetate Propionate Carboxylate; Ceteareth-7 Stearate; Cetearyl Behenate; Cetearyl Candelillate; Cetearyl Isononanoate; Cetearyl Octanoate; Cetearyl Palmitate; Cetearyl Stearate; Cetyl Acetate; Cetyl Acetyl Ricinoleate; Cetyl Caprylate; Cetyl C12-15-Pareth-9 Carboxylate; Cetyl Glycol Isostearate; Cetyl Isononanoate; Cetyl Lactate; Cetyl Laurate; Cetyl Myristate; Cetyl Octanoate; Cetyl Oleate; Cetyl Palmitate; Cetyl PCA; Cetyl PPG-2 Isodeceth-7 Carboxylate; Cetyl Ricinoleate; Cetyl Ricinoleate Benzoate; Cetyl Stearate; C16-20 Glycol Isostearate; C20-30 Glycol Isostearate; C14-16 Glycol Palmitate; Chimyl Isostearate; Chimyl Stearate; Chlorogenic Acids; Cholesteryl Acetate; Cholesteryl/Behenyl/Octyldodecyl Lauroyl Glutamate; Cholesteryl Butyrate; Cholesteryl Dichlorobenzoate; Cholesteryl Hydroxystearate; Cholesteryl Isostearate; Cholesteryl Isostearyl Carbonate; Cholesteryl Lanolate; Cholesteryl Macadamiate; Cholesteryl Nonanoate; Cholesteryl/Octyldodecyl Lauroyl Glutamate; Cholesteryl Oleate; Cholesteryl Stearate; Cinnamyl Acetate; Cinoxate; Citronellyl Acetate; Coco-Caprylate/Caprate; Coco Rapeseedate; Cocoyl Ethyl Glucoside; Copper PCA Methylsilanol; Corylus Avellanna Ethyl Ester; C12-15 Pareth-9 Hydrogenated Tallowate; C11-15 Pareth-3 Oleate; C12-15 Pareth-12 Oleate; C11-15 Pareth-3 Stearate; C11-15 Pareth-12 Stearate; Decyl Isostearate; Decyl Myristate; Decyl Oleate; Decyl Succinate; DEDM Hydantoin Dilaurate; Dextrin Behenate; Dextrin Laurate; Dextrin Myristate; Dextrin Palmitate; Dextrin Stearate; Diacetin; Dibutyl Adipate; Dibutyl Oxalate; Dibutyl Phthalate; Dibutyl Sebacate; D1-C12-15 Alkyl Adipate; D1-C12-15 Alkyl Fumarate; Di-C12-13 Alkyl Malate; D1-C12-13 Alkyl Tartrate; D1-C14-15 Alkyl Tartrate; Dicapryl Adipate; Dicaprylyl Maleate; Dicetearyl Dimer Dilinoleate; Dicetyl Adipate; Dicetyl Thiodipropionate; Dicocoyl Pentaerythrilyl Distearyl Citrate; Diethoxyethyl Succinate; Diethyl Acetyl Aspartate; Diethylaminoethyl Cocoate; Diethylaminoethyl PEG-5 Cocoate; Diethylaminoethyl PEG-5 Laurate; Diethylaminoethyl Stearate; Diethyl Aspartate; Diethylene Glycol Dibenzoate; Diethylene Glycol Diisononanoate; Diethylene Glycol Dioctanoate; Diethylene Glycol Dioctanoate/Diisononanoate; Diethyl Glutamate; Diethyl Oxalate; Diethyl Palmitoyl Aspartate; Diethyl Phthalate; Diethyl Sebacate; Diethyl Succinate; Digalloyl Trioleate; Diglyceryl Stearate Malate; Dihexyl Adipate; Dihexyldecyl Lauroyl Glutamate; Dihydroabietyl Behenate; Dihydroabietyl Methacrylate; Dihydrocholesteryl Butyrate; Dihydrocholesteryl Isostearate; Dihydrocholesteryl Macadamiate; Dihydrocholesteryl Nonanoate; Dihydrocholesteryl Octyldecanoate; Dihydrocholesteryl Oleate; Dihydrogenated Palmoyl Hydroxyethylmonium Methosulfate; Dihydrogenated Tallow Phthalate; Dihydrophytosteryl Octyldecanoate; Dihydroxyethylamino Hydroxypropyl Oleate; Dihydroxyethyl Soyamine Dioleate; Diisobutyl Adipate; Diisobutyl Oxalate; Diisocetyl Adipate; Diisodecyl Adipate; Diisopropyl Adipate; Diisopropyl Dimer Dilinoleate; Diisopropyl Methyl Cinnamate; Diisopropyl Oxalate; Diisopropyl Sebacate; Diisostearamidopropyl Epoxypropylmonium Chloride; Diisostearoyl Trimethylolpropane Siloxy Silicate; Diisostearyl Adipate; Diisostearyl Dimer Dilinoleate; Diisostearyl Fumarate; Diisostearyl Glutarate; Diisostearyl Malte; Dilaureth-7 Citrate; Dilauryl Thiodipropionate; Dimethicone Copolyol Acetate; Dimethicone Copolyol Adipate; Dimethicone Copolyol Almondate; Dimethicone Copolyol Beeswax; Dimethicone Copolyol Behenate; Dimethicone Copolyol Benzoate; Dimethicone Copolyol Borageate; Dimethicone Copolyol Cocoa Butterate; Dimethicone Copolyol Dhupa Butterate; Dimethicone Copolyol Hydroxystearate; Dimethicone Copolyol Isostearate; Dimethicone Copolyol Kokum Butterate; Dimethicone Copolyol Lactate; Dimethicone Copolyol Laurate; Dimethicone Copolyol Mango Butterate; Dimethicone Copolyol Meadowfoamate; Dimethicone Copolyol Mohwa Butterate; Dimethicone Copolyol Octyldodecyl Citrate; Dimethicone Copolyol Olivate; Dimethicone Copolyol Phthalate; Dimethicone Copolyol Sal Butterate; Dimethicone Copolyol Shea Butterate; Dimethicone Copolyol Stearate; Dimethicone Copoly Undecylenate; Dimethiconol Beeswax; Dimethiconol Behenate; Dimethiconol Borageate; Dimethiconol Dhupa Butterate; Dimethiconol Fluoroalcohol Dillnoleic Acid; Dimethiconol Hydroxystearate; Dimethiconol Illipe Butterate; Dimethiconol Isostearate; Dimethiconol Kokum Butterate; Dimethiconol Lactate; Dimethiconol Mohwa Butterate; Dimethiconol Sal Butterate; Dimethiconol Stearate; Dimethyl Adipate; Dimethylaminoethyl Methacrylate; Dimethyl Brassylate; Dimethyl Cystinate; Dimethyl Glutarate; Dimethyl Maleate; Dimethyl Oxalate; Dimethyl Phthalate; Dimethyl Succinate; Dimyristyl Tartrate; Dimyristyl Thiodipropionate; Dinonoxynol-9 Citrate; Dioctyl Adipate; Dioctyl Butamido Triazone; Dioctyl Dimer Dilinoleate; Dioctyldodeceth-2 Lauroyl Glutamate; Dioctyldodecyl Adipate; Dioctyldodecyl Dimer Dilinoleate; Dioctyldodecyl Dodecanedioate; Dioctyldodecyl Fluoroheptyl Citrate; Dioctyldodecyl Lauroyl Glutamate; Dioctyldodecyl Stearoyl Dimer Dilinoleate; Dioctydodecyl Stearoyl Glutamate; Dioctyl Fumarate; Dioctyl Malate; Dioctyl Maleate; Dioctyl Phthalate; Dioctyl Sebacate; Dioctyl Succinate; Dioleoyl Edetolmonium Methosulfate; Dipalmitoyl Hydroxyproline; Dipentaerythrityl Hexacaprylate/Hexacaprate; Dipentaerythrityl Hexaheptanoate/Hexacaprylate/Hexacaprate; Dipentaerythrityl Hexahydroxystearate; Dipentaerythrityl Hexahydroxystearate/Stearate/Rosinate; Dipentaerythrityl Hexaoctanoate/Behenate; Dipentaerythrityl Pentahydroxystearate/Isostearat-e; Diphenyl Carbomethoxy Acetoxy Naphthopyran; Dipropyl Adipate; Dipropylene Glycol Caprylate; Dipropylene Glycol Dibenzoate; Dipropylene Glycol Salicylate; Dipropyl Oxalate; Disodium Laureth-7 Citrate; Disodium PEG-5 Laurylcitrate Sulfosuccinate; Disodium PEG-8 Ricinosuccinate; Disodium Succinoyl Glycyrrhetinate; Disodium 2-Sulfolaurate; Disteareth-2 Lauroyl Glutamate; Disteareth-5 Lauroyl Glutamate; Distearyl Thiodipropionate; Ditallowoylethyl Hydroxyethylmonium Methosulfate; Ditridecyl Adipate; Ditridecyl Dimer Dilinoleate; Ditridecyl Thiodipropionate; Dodecyl Gallate; Erucyl Arachidate; Erucyl Erucate; Erucyl Oleate; Ethiodized Oil; Ethoxydiglycol Acetate; Ethoxyethanol Acetate; Ethyl Acetate; Ethyl Almondate; Ethyl Apricot Kernelate; Ethyl Arachidonate; Ethyl Aspartate; Ethyl Avocadate; Ethyl Benzoate; Ethyl Biotinate; Ethyl Butylacetylaminopropionate; Ethyl Cinnamate; Ethyl Cyanoacrylate; Ethyl Cyclolhexyl Propionate; Ethyl Digydroxypropyl PABA; Dethyl Diisopropylcinnamate; Ethylene Brassylate; Ethylene Carbonate; Ethyl Ester of Hydrolyzed Animal Protein; Ethyl Ester of Hydrolyzed Keratin; Ethyl Ester of Hydrolyzed Silk; Ethyl Ester of PVM/MA Copolymer; Ethyl Ferulate; Ethyl Glutamate; Ethyl Isostearate; Ethyl Lactate; Ethyl Laurate; Ethyl Linoleate; Ethyl Linolenate; Ethyl Methacrylate; Ethyl Methoxycinnamate; Ethyl Methylphenylglycidate; Ethyl Minkate; Ethyl Morrhuate; Ethyl Myristate; Ethyl Nicotinate; Ethyl Oleate; Ethyl Olivate; Ethyl PABA Ethyl Palmitate; Ethylparaben; Ethyl PCA; Ethyl Pelargonate; Ethyl Persate; Ethyl Phenylacetate; Ethyl Ricinoleate; Ethyl Serinate; Ethyl Stearate; Ethyl Thioglycolate; Ethyl Urocanate; Ethyl Wheat Germate; Ethyl Ximenynate; Etocrylene; Farnesyl Acetate; Galactonolactone; Galbanum (Ferula Galbaniflua) Oil; Gamma-Nonalacione; Geranyl Acetate; Glucarolactone; Glucose Glutamate; Glucose Pentaacetate; Glucuronolactone; Glycereth-7 Benzoate; Glycereth-7 Diisononanoate; Glycereth-8 Hydroxystearate; Glycereth-5 Lactate; Glycereth-25 PCA Isostearate; Glycereth-7 Triacetate; Glyceryl Triacetyl Hydroxystearate; Glyceryl Triacetyl Ricinoleate; Glycolamide Stearate; Glycol/Butylene Glycol Montanate; Glycol Catearate; Glycol Dibehenate; Glycol Dilaurate; Glycol Dioctanoate; Glycol Dioleate; Glycol Distearate; Glycol Ditallowate; Glycol Hydroxystearate; Glycol Montanate; Glycol Octanoate; Glycol Oleate; Glycol Palmitate; Glycol Ricinoleate; Glycol Salicylate; Glycol Stearate; Glycol Stearate SE; Glycyrrhetinyl Stearate; Hexacosyl Glycol Isostearate; Hexanediol Beeswax; Hexanediol Distearate; Hexanetriol Beeswax; Hexyldecyl Benzoate; Hexyldecyl Ester of Hydrolyzed Collagen; Hexyldecyl Isostearate; Hexyldecyl Laurate; Hexyldecyl Octanoate; Hexyldecyl Oleate; Hexyldecyl Palmitate; Hexyldecyl Stearate; Hexyldodecyl Salicylate; Hexyl Isostearate; Hexyl Laurate; Hexyl Nicotinate; Homosalate; Hydrogenated Castor Oil Hydroxystearate; Hydrogenated Castor Oil Isostearate; Hydrogenated Castor Oil Laurate; Hydrogenated Castor Oil Stearate; Hydrogenated Castor Oil Triisostearate; Hydrogenated Methyl Abietate; Hydrogenated Rosin; Hydroquinone PCA; Hydroxycetyl Isostearate; Hydroxyoctacosanyl Hydroxystearate; Inositol Hexa-PCA; Iodopropynyl Butylcarbamate; Isoamyl Acetate; Isoamyl Laurate; Isoamyl p-Methoxycinnamate; Isobutyl Acetate; Isobutylated Lanolin Oil; Isobutyl Benzoate; Isobutyl Myristate; Isobutyl Palmitate; Isobutylparaben; Isobutyl Pelargonate; Isobutyl Stearate; Isobutyl Tallowate; Isoceteareth-8 Stearate; Isoceteth-10 Stearate; Isocetyl Behenate; Isocetyl Isodecanoate; Isocetyl Isostearate; Isocetyl Laurate; Isocetyl Linoleoyl Stearate; Isocetyl Myristate; Isocetyl Octanoate; Isocetyl Palmitate; Isocetyl Salicylate; Isocetyl Stearate; Isocetyl Stearoyl Stearate; Isodeceth-2 Cocoate; Isodecyl Citrate; Isodecyl Cocoate; Isodecyl Hydroxystearate; Isodecyl Isononanoate; Isodecyl Laurate; Isodecyl Myristate; Isodecyl Neopentanoate; Isodecyl Octanoate; Isodecyl Oleate; Isodecyl Palmitate; Isodecylparaben; Isodecyl Salicylate; Isodecyl Stearate; Isohexyl Laurate; Isohexyl Neopentanoate; Isohexyl Palmitate; Isolauryl Behenate; Isomerized Jojoba Oil; Isononyl Ferulate; Isooctyl Thioglycolate; Isopropyl Acetate; Isopropyl Arachidate; Isopropyl Avocadate; Isopropyl Behenate; Isopropyl Benzoate; Isopropylbenzyl Salicylate; Isopropyl Citrate; Isopropyl C12-15-Pareth-9 Carboxylate; Isopropyl Hydroxystearate; Isopropyl Isostearate; Isopropyl Jojobate; Isopropyl Lanolate; Isopropyl Laurate; Isopropyl Linoleate; Isopropyl Myristate; Isopropyl Oleate; Isopropylparaben; Isopropyl PPG-2-Isodeceth-7 Carboxylate; Isopropyl Ricinoleate; Isopropyl Sorbate; Isopropyl Stearate; Isopropyl Tallowate; Isopropyl Thioglycolate; Isosorbide Laurate; Isosteareth-10 Stearate; Isostearyl Avocadate; Isostearyl Behenate; Isostearyl Benzoate; Isostearyl Erucate; Isostearyl Isononanoate; Isostearyl Isostearate; Isostearyl Isostearoyl Stearate; Isostearyl Lactate; Isostearyl Laurate; Isostearyl Myristate; Isostearyl Neopentanoate; Isostearyl Octanoate; Isostearyl Palmitate; Isostearyl Stearoyl Stearate; Isotridecyl Isononanoate; Isotridecyl Laurate; Isotridecyl Myristate; Jojoba (Buxus Chinensis) Oil; Jojoba Esters; Kojic Dipalmitate; Laneth-9 Acetate; Laneth-10 Acetate; Laneth-4 Phosphate; Lanolin Linoleate; Lanolin. Ricinoleate; Laureth-2 Acetate; Laureth-2 Benzoate; Laureth-6 Citrate; Laureth-7

Citrate; Laureth-2 Octanoate; Laureth-7 Tartrate; Lauroyl Ethyl Glucoside; Lauroyl Lactylic Acid; Lauryl Behenate; Lauryl Cocoate; Lauryl Isostearate; Lauryl Lactate; Lauryl Methacrylate; Lauryl Myristate; Lauryl Octanoate; Lauryl Oleate; Lauryl Palmitate; Lauryl Stearate; Linalyl Acetate; Linoleyl Lactate; Madecassicoside; Mannitan Laurate; Mannitan Oleate; Menthyl Acetate; Menthyl Anthranilate; Menthyl Lactate; Menthyl PCA; Menthyl Salicylate; Methoxyisopropyl Acetate; Methoxy-PEG-7 Rutinyl Succinate; Methyl Acetate; Methyl Acetyl Ricinoleate; Methyl Anthranilate; Methyl Behenate; Methyl Benzoate; Methyl Caproate; Methyl Caprylate; Methyl Caprylate/Caprate; Methyl Cocoate; 6-Methyl Coumarin; Methyl Dehydroabietate; Methyl Dihydroabietate; Methyldihydrojasmonate; Methyl Gluceth-20 Benzoate; Methyl Glucose Dioleate; Methyl Glucose Isostearate; Methyl Glucose Laurate; Methyl Glucose Sesquicaprylate/Sesquicaprate; Methyl Glucose Sesquicocoate; Methyl Glucose Sesquiisostearate; Methyl Glucose Sesquilaurate; Methyl Glucose Sesquioleate; Methyl Glucose Sesquistearate; Methyl Glycyrrhizate; Methyl Hydrogenated Rosinate; Methyl Hydroxystearate; Methyl Isostearate; Methyl Laurate; Methyl Linoleate; Methyl 3-Methylresorcylate; Methyl Myristate; Methyl Nicotinate; Methyl Oleate; Methyl Palmate; Methyl Palmitate; Methylparaben; Methyl Pelargonate; Methyl Ricinoleate; Methyl Rosinate; Methyl Salicylate; Methylsilanol Acetylmethionate; Methylsilanol Carboxymethyl Theophylline; Methylsilanol Carboxymethyl Theophylline Alginate; Methylsilanol Hydroxyproline; Methylsilanol Hydroxyproline Aspartate; Methylsilanol Mannuronate; Methylsilanol PCA; Methyl Soyate; Methyl Stearate; Methyl Thioglycolate; Monosaccharide Lactate Condensata; Myreth-3 Caprate; Myreth-3 Laurate; Myreth-2 Myristate; Myreth-3 Myristate; Myreth-3 Octanoate; Myreth-3 Palmitate; Myristoyl Ethyl Glucoside; Myristoyl Lactylic Acid; Myristyl Isostearate; Myristyl Lactate; Myristyl Lignocerate; Myristyl Myristate; Myristyl Octanoate; Myristyl Propionate; Myristyl Salicylate; Myristyl Stearate; Neopentyl Glycol Dicaprate; Neopentyl Glycol Dicaprylate/Dicaprate; Neopentyl Glycol Dicaprylate/Dipelargonate/Dicaprate; Neopentyl Glycol Diheptanoate; Neopentyl Glycol Diisostearate; Neopentyl Glycol Dilaurate; Neopentyl Glycol Dioctanoate; Nonyl Acetate; Nopyl Acetate; Octacosanyl Glycol Isostearate; Octocrylene; Octyl Acetoxystearate; Octyl Benzoate; Octyl Caprylate/Caprate; Octyl Cocoate; Octyldecyl Oleate; Octyldodecyl Behenate; Octyldodecyl Benzoate; Octyldodecyl Erucate; Octyldodecyl Hydroxystearate; Octyldodecyl Isostearate; Octyldodecyl Lactate; Octyldodecyl Lanolate; Octyldodecyl Meadowfoamate; Octyldodecyl Myristate; Octyldodecyl Neodecanoate; Octyldodecyl Neopentanoate; Octyldodecyl Octanoate; Octyldodecyl Octyldodecanoate; Octyldodecyl Oleate; Octyldodecyl Olivate; Octyldodecyl Ricinoleate; Octyldodecyl Stearate; Octyldodecyl Steroyl Stearate; Octyl Gallate; Octyl Hydroxystearate; Octyl Hydroxystearate Benzoate; Octyl Isononanoate; Octyl Isopalmitate; Octyl Isostearate; Octyl Laurate; Octyl Linoleayl Stearate; Octyl Methoxycinnamate; Octyl Myristate; Octyl Neopentanoate; Octyl Octanoate; Octyl Oleate; Octyl Palmitate; Octyl PCA; Octyl Pelargonate; Octyl Salicylate; Octyl Stearate; Oleoyl Ethyl Glucoside; Oleth-2 Benzoate; Oleyl Acetate; Oleyl Arachidate; Oleyl Erucate; Oleyl Ethyl Phosphate; Oleyl Lactate; Oleyl Lanolate; Oleyl Linoleate; Oleyl Myristate; Oleyl Oleate; Oleyl Phosphate; Oleyl Stearate; Oryzanol; Ozonized Jojoba Oil; Palmitoyl Carniline; Palmitoyl Inulin; Palmitoyl Myristyl Serinate; Pantethine; Panthenyl Ethyl Ester Acetate; Panthenyl Triacetate; PCA Glyceryl Oleate; Pea Palmitate; PEG-18 Castor Oil Dioleate; PEG-5 DEDM Hydantoin Oleate; PEG-15 DEDM Hydantoin Stearate;

PEG-30 Dipolyhydroxystearate; PEG-20 Hydrogenated Castor Oil Isostearate; PEG-50 Hydrogenated Castor Oil Isostearate; PEG-20 Hydrogenated Castor Oil Triisostearate; PEG-20 Mannitan Laurate; PEG-20 Methyl Glucose Distearate; PEG-80 Methyl Glucose Laurate; PEG-20 Methyl Glucose Sesquicaprylate/Sesquicaprate; PEG-20 Methyl Glucose Sesquilaurate; PEG-5 Oleamide Dioleate; PEG-150 Pentaerythrityl Tetrastearate; PEG-3/PPG-2 Glyceryl/Sorbitol Hydroxystearate/Isostearate; PEG-4 Proline Linoleate; PEG-4 Proline Linolenate; PEG-8 Propylene Glycol Cocoate; PEG-55 Propylene Glycol Oleate; PEG-25 Propylene Glycol Stearate; PEG-75 Propylene Glycol Stearate; PEG-120 Propylene Glycol Stearate; PEG-40 Sorbitol Hexaoleate; PEG-50 Sorbitol Hexaoleate; PEG-30 Sorbitol Tetraoleate Laurate; PEG-60 Sorbitol Tetrastearate; PEG-5 Tricapryl Citrate; PEG-5 Tricetyl Citrate; PEG-5 Trilauryl Citrate; PEG-5 Trimethylolpropane Trimyristate; PEG-5 Trimyristyl Citrate; PEG-5 Tristearyl Citrate; PEG-6 Undecylenate; Pentadecalacione; Pentaerythrityl Dioleate; Pentaerythrityl Distearate; Pentaerythrityl Hydrogenated Rosinate; Pentaerythrityl Isostearate/Caprate/Caprylate/Adipate; Pentaerythrityl Rosinate; Pentaerythrityl Stearate; Pentaerythrityl Stearate/Caprate/Caprylate/Adipate; Pentaerythrityl Stearate/Isostearate/Adipate/Hydroxystearate; Pentaerythrityl Tetraabietate; Pentaerythrityl Tetraacetate; Pentaerythrityl Tetrabehenate; Pentaerythrityl Tetrabenzoate; Petaerythrityl Tetracaprylate/Tetracaprate; Pentaerythrityl Tetracocoate; Pentaerythrityl Tetraisononanoate; Pentaerythrityl Tetralaurate; Pentaerythrityl Tetramyristate; Pentaerythrityl Tetraoctanoate; Pentaerythrityl Tetraoleate; Pentaerythrityl Tetrapelargonate; Petaerythrityl Tetrastearate; Pentaerythrityl Trioleate; Phenethyl Acetate; Phenolphthalein; Phenoxyethylparaben; Phenyl Benzoate; Phenylparaben; Phenyl Salicylate; Phylosteryl Macadamiate; Poloxamer 105 Benzoate; Poloxamer 182 Dibenzoate; Polycaprolactone; Polydimethylaminoethyl Methacrylate; Polyethylacrylate; Polyethylglutamate; Polyethylmethacrylate; Polymethyl Acrylate; Polymethylglutamate; Polysorbate 80 Acetate; Polyvinyl Acetate; Potassium Butylparaben; Potassium Deceth-4 Phosphate; Potassiu Ethylparaben; Potassium Methylparaben; Potassium Propylparaben; PPG-2 Isoceleth-20 Acetate; PPG-14 Laureth-60 Alkyl Dicarbamate; PPG-20 Methyl Glucose Ether Acetate; PPG-20 Methyl Glucose Ether Distearate; PPG-2 Myristyl Ether Propionate; PPG-14 Palmeth-60 Alkyl Dicarbamate; PPG-15 Steryl Ether Benzoate; Pregnenolone Acetate; Propyl Acetate; Propyl Benzoate; Propylene Carbonate; Propylene Glocol Alginate; Propylene Glycol Behenate; Propylene Glycol Caprylate; Propylene Glycol Ceteth-3 Acetate; Propylene Glycol Ceteth-3 Propionate; Propylene Glycol Citrate; Propylene Glycol Cocoate; Propylene Glycol Dicaprate; Propylene Glycol Dicaproate; Propylene Glycol Dicaprylate; Propylene Glycol Dicocoate; Propylene Glycol Diisononanoate; Propylene Glycol Diisostearate; Propylene Glycol Dilaurate; Propylene Glycol Dioctanoate; Propylene Glycol Dioleate; Propylene Glycol Dipelargonate; Propylene Glycol Distearate; Propylene Glycol Diundecanoate; Propylene Glycol Hydroxystearate; Propylene GlycolIsoceteth-3 Acetate; Propylene Glycol Isostearate; Propylene Glycol Laurate; Propylene Glycol Linoleate; Propylene Glycol Linolenate; Propylene Glycol Myristate; Propylene Glycol Myristyl Ether Acetate; Propylene Glycol Oleate; Propylene Glycol Oleate SE; Propylene Glycol Ricinoleate; Propylene Glycol Soyate; Propylene Glycol Stearate; Propylene Glycol Stearate SE; Propyl Gallate; Propylparaben; Pyricarbate; Pyridoxine Dicaprylate;

Pyridoxine Dilaurate; Pyridoxine Dioctenoate; Pyridoxine Dipalmitate; Pyridoxine Glycyrrhetinate; Pyridoxine Tripalmitate; Raffinose Myristate; Raffinose Oleate; Resorcinol Acetate; Retinyl Acetate; Retinyl Linoleate; Retinyl Palmitate; Retinyl Propionate; Riboflavin Tetraacetate; Ribonolaclone; Rosin Acrylate; Siloxanetriol Phytate; Silybum Marianum Ethyl Ester; Sodium Behenoyl Lactylate; Sodium Butylparaben; Sodium Caproyl Lactylate; Sodium Cocoyl Lactylate; Sodium Dilaureth-7 Citrate; Sodium Ethylparaben; Sodium Ethyl 2-Sulfolaurate; Sodium Isostearoyl Lactylate; Sodium Laureth-7 Tartrate; Sodium Lauroyl Lectylate; Sodium Methylparaben; Sodium Methyl 2-Sulfolaurate; Sodium Oleoyl Lactylate; Sodium Panteheine Sulfonate; Sodium Phytate; Sodium Propylparaben; Sodium Stearoyl Lactylate; Sorbeth-2 Cocoate; Sorbeth-6 Hexastearate; Sorbeth-3 Isostearate; Sorbityl Acetate; Soybean Palmitate; Soy Sterol Acetate; Stearamide DEA-Distearate; Stearamide DIBA-Stearate; Stearamide MEA-Stearate; Steareth-5 Stearate; Stearoyl Lactylic Acid; Stearyl Acetate; Stearyl Acetyl Glutamate; Stearyl Beeswax; Stearyl Behenate; Stearyl Benzoate; Stearyl Caprylate; Stearyl Citrate; Stearyl Erucate; Stearyl Glycol Isostearate; Stearyl Glycyrrhetinate; Stearyl Heptanoate; Stearyl Lactate; Stearyl Linoleate; Stearyl Octanoate; Stearyl Stearate; Stearyl Stearoyl Stearate; Sucrose Acetate Isobutyrate; Sucrose Benzoate; Sucrose Cocoate; Sucrose Dilaurate; Sucrose Distearate; Sucrose Laurate; Sucrose Myristate; Sucrose Octaacetate; Sucrose Oleate; Sucrose Palmitate; Sucrose Polybehenate; Sucrose Polycottonseedate; Sucrose Polylaurate; Sucrose Polylinoleate; Sucrose Polypalmate; Sucrose Polysoyate; Sucrose Polystearate; Sucrose Ricinoleate; Sucrose Stearate; Sucrose Tetrastearate Triacetate; Sucrose Tribehenate; Sucrose Tristearate; Tallowoyl Ethyl Glucoside; Tannic Acid; TEA-Lauroyl Lactylate; Telmesteine; Terpineol Acetate; Tetrabutyl Phenyl Hydroxybenzoate; Tetradecyleicosyl Stearate; Tetrahexyldecyl Ascorbate; Tetrahydrofurfuryl Acetate; Tetrahydrofurfuryl Ricinoleate; Tocophersolan; Tocopheryl Acetate; Tocopheryl Linoleate; Tocopheryl Linoleate/Oleate; Tocopheryl Nicotinate; Tocopheryl Succinate; Tributyl Citrate; Tri-C12-13 Alkyl Citrate; Tri-C14-15 Alkyl Citrate; Tricaprylyl Citrate; Tridecyl Behenate; Tridecyl Cocoate; Tridecyl Erucate; Tridecyl Isononanoate; Tridecyl Laurate; Tridecyl Myristate; Tridecyl Neopentanoate; Tridecyl Octanoate; Tridecyl Stearate; Tridecyl Stearoyl Stearate; Tridecyl Trimellitate; Triethyl Citrate; Triethylene Glycol hydrogenated Rosinate; Trihexyldecyl Citrate; Triisocetyl Citrate; Triisopropyl Citrate; Triisopropyl Trilinoleate; Triisostearyl Citrate; Triisostearyl Trilinoleate; Trilactin; Trilauryl Citrate; Trimethylolpropane Tricaprylate/Tricaprate; Trimethylolpropane Tricocoate; Trimethylolpropane Trilaurate; Trimethylalpropane Trioctanoate; Trimethylolpropane Tristearate; Trimethyl Pentanyl Diisobutyrate; Trioctyl Citrate; Trioctyldodecyl Borate; Trictyl Trimellitate; Trioleyl Citrate; TriPABA Panthenol; Tripropylene Glycol Citrate; Tristearyl Citrate; Tristearyl Phosphate; Vinyl Acetate; and Yeast Palmitate.

In addition to esters, alcohols may be gelled to form a gelled alcohol by using a diblock copolymer, a triblock copolymer, a star polymer, a radial polymer, a multi-block copolymer, and mixtures thereof. Suitable alcohols also may be gelled by alkyl galactomannan, polybutadiene, or other aforementioned polymers. Any alcohols as represented by the following formula may be gelled in embodiments of the invention.

where R represents any organic functional group which includes, but is not limited to, hydrocarbyl, phenyl, methoxyphenyl, and alkylphenyl, substituted alkyl, substituted phenyl, etc. Preferred alcohols include, but are not limited to, isostearyl alcohol, and octyl dodecanol. Other suitable alcohols include, but are not limited to, Abietyl Alcohol; Arachidyl Alcohol; Batyl Alcohol; Behenyl Alcohol; Benzyl Alcohol; Bishydroxyethyl Biscetyl Malonamide; Borneol; 2-t-Butylcyclohexyloxybutan-ol; Butyloctanol; C9-11 Alcohol; C12-13 Alcohol; C12-15 Alcohol; C12-16 Alcohol; C14-15 Alcohol; C-20-40 Alcohols; C30-50 Alcohols; C40-60 Alcohols; C18-38 Alkyl Hydroxystearoyl Stearate; Camphylcyclohexanol; Caproyl Sphingosine; Caprylic Alcohol; Caprylyl Glycol; CD Alcohol 19; Ceramide 1; Ceramide 2; Cermide 3; Ceramide 4; Ceramide 5; Ceramide 1A; Ceramide 6 II; Cetearyl Alcohol; Cetyl Alcohol; Cetylarachidol; Cetyl Glycol; C9-13 Fluoroalcohol; C14-18 Glycol; C15-18 Glycol; C18-30 Glycol; C20-30 Glycol; Chimyl Alcohol; Chlorphenesin; Cholecidiferol; Cholesterol; Cinnamyl Alcohol; Citronellol; Coconut Alcohol; Decyl Alcohol; Decyltetradecanol; 7-Dehydrocholesterol; Dichlorobenzyl Alcohol; Dihydrocholesterol; Dihydrolanosterol; Dihydroxyacetone; Dihydroxyethylamino Hydroxypropyl Oleate; 2,6-Dimethyl-7-Octen-2-ol; Dimethyl Octynediol; Dimethyl Phenylpropanol; Dodecylhexadecanol; Dodecyltetradecanol; Ergocalciferol; Ethyl Hexanediol; Farnesol; Galactonolactone; Geraniol; Glycyrrhetinic Acid; Glycyrrhizic Acid; Heptylundecanol; Hexacosyl Glycol; 3-Hexenol; Hexyl Alcohol; Hexyldecanol; Hexyldecyloctadecanol; Hexylene Glycol; Hinokitiol; Hydroabietyl Alcohol; Hydrogenated Ethylbicycloneplane Guaiacol; Hydrogenated Tallow Alcohol; Hydrolyzed Glycyrrhizinate; Hydroxycapric Acid; Hydroxycaproyl Phytosphingosine; Hydroxycaprylic Acid; Hydroxycapryloyl Phytosphingosine; Hydroxyethyl Palmityl Oxyhydroxypropyl Palmitamide; Hydroxylauric Acid; Hydroxylauroyl Phytosphingosine; Hydroxymethyl Dioxoazabicyclooctane; Hydroxyproline; Hydroxystearyl Cetyl Ether; Jojoba Alcohol; Lactoyl Phytosphingosine; Lanolin Alcohol; Lauryl Alcohol; Lauryl Glycol; Linalool; p-Menthan-7-ol; Menthol; Menthone Glycerin Acetal; 3-Methylamino-4-Nitrophenoxyethanol; Methyl Glycyrrhiziate; Methylsilanol Hydroxyproline; Myricyl Alcohol; Myristyl Alcohol; Nicotinyl Alcohol; Nicotinyl Tartrate; 3-Nitro-4-Aminophenoxyeth-anol; Octacosanyl Glycol; Octoxyglycerin; Octoxyglyceryl Behenate; Octyldodecanol; 2-Oeamido-1,3-Octadecanediol; Oleyl Alcohol; Palm Alcohol; Palm Kernel Alcohol; Palmitamidohexadecanediol; Panthenol; Panthenyl Ethyl Ether; Panthenyl Hydroxypropyl Steardimonium Chloride; Pentadecyl Alcohol; Pentylene Glycol; Phenethyl Alcohol; Phenoxyethanol; Phenoxyisopropanol; Phenylisohexanol; Phenylpropanol; Phytosphingosine; Polyvinyl Alcohol; Propanediol; Propyl Alcohol; Propylene Glycol; Pyridoxine Glycyrrhetinate; Retinol; Ribonolactone; N-Stearoyl-Dihydroshingosine; Stearyl Alcohol; Stearyl Glycol; Tallow Alcohol; Terpineol; Tetradecyleicosanol; Tetradecyloctadecanol; Tetrahydrofurfuryl Alcohol; Tetramethyl Cyclopentene Butenol; Tetramethyl Decynediol; Tridecyl Alcohol; Trimethylhexanol; Troxerutin; Undeceth-3; Undecylenyl Alcohol; and Undecylpentadecanol.

Numerous ethers also may be gelled to form gelled ether compositions by using a diblock copolymer, triblock copolymer, star polymer, radial polymer, multi-block copolymer, or mixtures thereof. Suitable ethers also may be gelled by alkyl galactomannan, polybutadiene, or other aforementioned polymers. Generally, an ether compound is represented by the following formula:

where R and R' individually include, but are not limited to, hydrocarbyl, phenyl, methoxyphenyl, alkylphenyl, substituted alkyl, substituted phenyl, etc. Preferred ethers include, but are not limited to, dicarylyl ether and octyl methoxycinnamate. Dicarylyl either is represented by the following chemical formula.

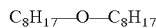

Other suitable ethers include, but are not limited to, Anethole; p-Anisic Acid; Batyl Alcohol; Batyl Isostearate; Batyl Stearate; Benzylhemiformal; 1,3-Bis-(2,4-Diaminophenoxy) propane; Butoxyethyl Acetate; Butoxyethyl Nicotinate; Butoxyethyl Stearate; Butoxypropanol; 2-t-Butylcyclohexyloxybutanol; Butyl Glucoside; Butylglucoside Caprate; Butyl Methoxydibenzoylmethane; Caprylyl/Capryl Glucoside; Capsaicin; Carboxymethyl Chitin; Carboxymethyl Chitosan Succinamide; Carboxymethyl Dextran; Cetearyl Glucoside; Cetyl Glyceryl Ether; Cetyl-PG Hydroxyethyl Decanamide; Cetyl-PG Hydroxyethyl Palmitamide; Chimyl Alcohol; Chimyl Isostearate; Chimyl Stearate; Chlorphenesin; Cinoxate; Cocamidopropyl Lauryl Ether; Coceth-4 Glucoside; Coco-Glucoside; Dibenzylidene Sorbitol; Dicetyl Ether; Dichlorophenyl Imidazoidioxolan; Dimethicone Copolyol Butyl Ether; Dimethicone Copolyol Ethyl Ether; Dimethicone Copolyol Methyl Ether; Dimethyl Hexahydronaphthyl Dihydroxymethyl Acetal; Dimethyl Isosorbide; Dioleyl Tocopheryl Methylsilanol; Diosmine; Disodium Cetyl Phenyl Ether Disulfonate; Disodium Decyl Phenyl Ether Disulfonate; Disodium Lauryl Phenyl Ether Disulfonate; Distarch Glyceryl Ether; Distearyl Ether; Ethoxydiglycol Acetate; Ethoxyheptyl Bicyclooctanone; 7-Ethylbicyclooxazolidine; Ethyl Methoxycinnamate; Ethyl Methylphenylglycidate; Ethyl Phenethyl Acetal; Eucalyptol; Eugenol; Ferulic Acid; Glyceryl Octanoate Dimethoxycinnamate; Glycofurol; Hexamethylindanopyran; Hexamidine; Hexamidine Diparaben; Hexamidine Paraben; Hydrogenated Ethylbicycloheptane Guaiacol; p-Hydroxyanisole; Hydroxydecyl Maltitol; Hydroxyethyl Glyceryl Oleate/Stearate; Hydroxyethyl Palmityl Oxyhydroxypropyl Palmitamide; Hydroxyethyl Sorbitol; Hydroxymethoxybenzyl Pelargonamide; Hydroxypropyl Starch Phosphate; Hydroxystearyl Cetyl Ether; Isobutyl Methyl Tetrahydropyranol; Isoeugenol; Isolongifolene Epoxide; Isopropyl Hydroxycetyl Ether; Isostearamidopropyl Epoxypropyl Dimonium Chloride; Isostearyl Glyceryl Ether; Isostearyl Glyceryl Pentaerythrityl Ether; Lauryl Polyglyceryl-6 Cetearyl Glycol Ether; Melatonin; Menthone Glycerin Acetal; Methoxylndane; Methoxyisopropyl Acetate; Methoxymethylbutanol; Methoxypropylgluconamide; Methylal; Ethyl Eugenol; Methyl Hexyl Ether; Methylsilanol Ascorbate; Myristyl-PG Hydroxyethyl Decanamide; 4-Nitroguaiacol; Octoxyglycerin; Octoxyglyceryl Behenate; Octoxyglyceryl Palmitate; Octyl Glyceryl Palmitate; Oleyl Glyceryl Ether; Panthenyl Ethyl Ether; Panthenyl Ethyl Ether Acetate; Panthenyl Hydroxypropyl Steardimonium Chloride; PEG-3 2,2-Di-p-Phenylenediamine; PEG-4 Ditallow Ether; PEG-150 Pentaerythrityl Tetrastearate; p-Phenetidine; Phenoxyethanol; Phenoxyethylparaben; Phenoxyisopropanol; Polyglycerin-3; Polyglycerin-4; Polyglycerin-6; Polyglycerin-10; Polyglyceryl-3 Cetyl Ether; Polyglyceryl-3 Decyltetradecyl Ether; Polyglyceryl-3 Hydroxylauryl Ether; Polyglyceryl-2 Lanolin Alcohol Ether; Polyglyceryl-4 Lauryl Ether; Polyglyceryl-2 Oleyl Ether; Polyglyceryl-4 Oleyl Ether; Polyglyceryl Sorbitol; Polyvinyl Methyl Ether; Polyvinyl Stearyl Ether; PPG-9 Diglyceryl Ether; PPG-1-PEG-9 Lauryl Glycol Ether; Propylene Glycol Myristyl Ether; Quassin; Silanetriol Trehalose Ether; TEA-Lauryl Ether; Tetrahydrodiferuloylmethane; Thiodiglycol; Triclosan; Triethylene Glycol; Trihydroxypalmitamidohydroxypropyl Myristyl Ether; Trimethoxycaprylylsilane; Troxerutin; and Ubiquinone.

Embodiments of the invention may also be used to obtain gelled natural products, such as naturally-occurring fats and oils. "Naturally-occurring fats and oils" often refer to the glyceryl esters of fatty acids (i.e., triglycerides) normally found in animal or plant tissues, including those which have been hydrogenated to reduce or eliminate unsaturation. Naturally occurring fats and oils include vegetable oils. Selected naturally-occurring fats and oils are represented by the following formula:

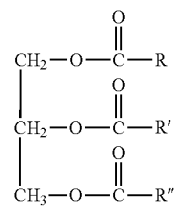

where R, R' and R" may be the same or different fatty acid radicals.

Suitable naturally-occurring fats and oils that may be gelled by using a diblock copolymer, triblock copolymer, star polymer, radial polymer, multi-block copolymer or mixtures thereof. Suitable naturally-occurring fats and oils also may be gelled by alkyl galactomannan, polybutadiene, or other aforementioned polymers. Examples of the suitable naturally-occurring fats and oils include, but are not limited to, *Adansonla Digitata* Oil; Apricot (*Prunus Armeniaca*) Kernel Oil; *Argania Spinosa* Oil; *Argemone Mexicana* Oil; Avocado (*Persea Gratissima*) Oil; Babassu (*Orbignya Olelfera*) Oil; Balm Mint (*Melissa Officinalis*) Seed Oil; Bitter Almond (*Prunus Amygdalus* Amara) Oil; Bitter Cherry (*Prunus Cerasus*) Oil; Black Currant (*Ribes Nigrum*) Oil; Borage (*Borago Officinalis*) Seed Oil; Brazil (*Bertholletia Excelsa*) Nut Oil; Burdock (*Arctium Lappa*) Seed Oil; Butter; C12-18 Acid Triglyceride; *Calophyllum Tacamahaca* Oil; *Camellia Kissi* Oil; *Camellia Oleifera* Seed Oil; Canola Oil; Caprylic/Capric/Lauric Triglyceride; Caprylic/Capric/Linoleic Triglyceride; Caprylic/Capric/Myristic/Stearic Triglyceride; Caprylic/Capric/Stearic Triglyceride; Caprylic/Capric Triglyceride; Caraway (*Carum Carvi*) Seed Oil; Carrot (*Daucus Carota Sativa*) Oil; Cashew (*Anacardium Occidentale*) Nut Oil; Castor Oil Benzoate; Castor (*Ricinus Communis*) Oil; Cephalins; Chaulmoogra (*Taraktogenos Kurzii*) Oil, Chia (*Salvia Hispanica*) Oil; Cocoa (*Theobrama Cocao*) Butter; Coconut (*Cocos Nucifera*) Oil; Cod Liver Oil; Coffee (*Coffea Arabica*) Oil; Corn (*Zea Mays*) Germ Oil; Corn (*Zea Mays*) Oil; Cottonseed (*Gossypium*) Oil; C10-18 Triglycerides; Cucumber (*Cucumis Sativus*) Oil; Dog Rose (*Rosa Canina*) Hips Oil; Egg Oil; Emu Oil; Epoxidized Soybean Oil; Evening Primrose (*Oenothera Biennis*) Oil; Fish Liver Oil; *Gevuina Avellana* Oil; Glyceryl Triacetyl Hydroxystearate; Glyceryl Triacetyl Ricinoleate; Glycolipids; Glycosphingolipids; Goat Butter; Grape (*Vitis Vinifera*) Seed Oil; Hazel (*Croylus Americana*) Nut Oil; Hazel (*Corylus Aveilana*) Nut Oil; Human Placental Lipids; Hybrid Safflower (*Carthamus Tinctorius*) Oil; Hybrid Sunflower (*Helianthus Annuus*) Seed Oil; Hydrogenated Canola Oil; Hydrogenated Castor Oil; Hydrogenated Castor Oil Laurate; Hydrogenated Castor Oil Triisostearate; Hydrogenated Coconut Oil; Hydrogenated Cottonseed Oil; Hydrogenated C12-18 Triglycerides; Hydrogenated Fish Oil; Hydrogenated Lard; Hydrogenated Menhaden Oil; Hydrogenated Milk Lipids; Hydrogenated Mink Oil; Hydrogenated Olive Oil; Hydrogenated Orange Roughy Oil; Hydrogenated Palm Kernel Oil; Hydrogenated Palm Oil; Hydrogenated Peanut Oil; Hydrogenated Rapeseed Oil; Hydrogenated Shark Liver Oil; Hydrogenated Soybean Oil; Hydrogenated Tallow; Hydrogenated Vegetable Oil; *Isatis Tinctoria* Oil; Job's Tears (*Coix Lacryma-Jobi*) Oil; Kiwi (*Actinidia Chinensis*) Seed Oil; Kukui (*Aleurites Moluccana*) Nut Oil; Lard; Lauric/Palmitic/Oleic Triglyceride; Linseed (*Linum Usitatissiumum*) Oil; Lupin (*Lupinus Albus*) Oil; *Macadamia Ternifolia* Nut Oil; Maleated Soybean Oil; Mango (*Mangifera Indica*) Seed Oil; Marmot Oil; Meadowfoam (*Limnanthes Alba*) Seed Oil; Menhaden Oil; Milk Lipids; Mink Oil; *Moringa Pterygosperma* Oil; *Mortierella* Oil; Musk Rose (*Rosa Moschata*) Seed Oil; Neatsfoot Oil; Neem (*Melia Azadirachta*) Seed Oil; Oat (*Avena Sativa*) Kernel Oil; Oleic/Linoleic Triglyceride; Oleic/Palmitic/Lauric/Myristic/L-inoleic Triglyceride; Oleostearine; Olive (*Olea Europaea*) Husk Oil; Olive (*Olea Europaea*) Oil; Omental Lipdis; Orange Roughy Oil; Ostrich Oil; Oxidized Corn Oil; Palm (*Elaeis Guineensis*) Kernel Oil; Palm (*Elaeis Guineensis*) Oil; Passionflower (*Passiflora Edulis*) Oil; Peach (*Prunus Persica*) Kernel Oil; Peanut (*Arachis Hypogaea*) Oil; Pecan (*Carya Illinoensis*) Oil; Pengawar Djambi (*Cibotium Barometz*) Oil; Phospholipids; Pistachio (*Pistacia Vera*) Nut Oil; Placental Lipids; Poppy (*Papaver Orientale*) Oil; Pumpkin (*Cucurbita Pepo*) Seed Oil; Quinoa (*Chenopodium Quinoa*) Oil; Rapeseed (*Brassica Campestris*) Oil; Rice (*Oryza Sativa*) Bran Oil; Rice (*Oryza Sativa*) Germ Oil; Safflower (*Carthamus Tinctorius*) Oil; Salmon Oil; Sandalwood (*Santalum Album*) Seed Oil; Seabuchthorn (*Hippophae Rhamnoides*) Oil; Sesame (*Sesamum Indicum*) Oil; Shark Liver Oil; Shea Butter (*Butyrospermum Parkii*); Silk Worm Lipids; Skin Lipids; Soybean (*Glycine Soja*) Oil; Soybean Lipid; Sphingolipids; Sunflower (*Helianthus Annuus*) Seed Oil; Sweet Almond (*Prunus Amygdalus Dulcis*) Oil; Sweet Cherry (*Prunus Avium*) Pit Oil; Tali Oil; Tallow; Tea Tree (*Melaleuca Alternifolia*) Oil; *Telphairia Pedata* Oil; Tomato (*Solanum Lycopersicum*) Oil; Triarachidin; Tribehenin; Tricaprin; Tricaprylin; *Trichodesma Zeylanicum* Oil; Trierucin; Triheptanoin; Triheptylundecanoin; Trihydroxymethoxystearin; Trihydroxystearin; Triisononanoin; Triisopalmitin; Triisostearin; Trilaurin; Trilinolein; Trilinolenin; Trimyristin; Trioctanoin; Triolein; Tripalmitin; Tripalmitolein; Triricinolein; Trisebacin; Tristearin; Triundecanoin; Tuna Oil; Vegetable Oil; Walnut (*Juglans Regia*) Oil; Wheat Bran Lipids; and Wheat (*Triticum Vulgare*) Germ Oil.

The gel compositions in accordance with embodiments of the invention may be obtained by the following method. First, one or more compounds to be gelled are mixed with a gelling agent. Second, the mixture typically is heated to a temperature in the range of about 70 degrees C. to about 140 degrees C., although other temperatures also are acceptable. The mixture is agitated until a homogeneous mixture is obtained. The homogeneous mixture is then cooled to room temperature. A gel composition is thus obtained. It is noted that the compound to be gelled need not be mixed with a gelling agent before heating. Instead, the compound may be heated to a desired temperature first, and then the gelling agent is added to the compound.

The following examples are given to illustrate embodiments of the invention. They are merely exemplary and are not intended to limit the scope of the invention otherwise described herein. All numerical values disclosed herein are approximate numbers. In some examples, an antioxidant was added in an amount of about 0.02%. Any antioxidants can be used. One suitable antioxidant is 2,6-di-tert-butyl-4-methylphenol ("BHT").

Example 1

A sample of gelled isopropyl myristate (available under the trade name of Estol 1512, Lexol IPM, etc.) was prepared (85.28 wt. % isopropyl myristate+14.30 wt. % Kraton G 1702+0.40 wt. % Kraton G 1650). The finished gel exhibited excellent clarity and had a Brookfield viscosity (5 rpm, spindle T-C) of 157,000 CPS at 25.° C.

Example 2

A sample of gelled octyl methoxycinnamate (trade names: Parsol MCX, Escalol 557, Neo Heliopan AV) was prepared (87.58 wt. % octyl methoxycinnamate+12.00 wt. % Kraton G 1701+0.40 wt. % Kraton G 1650). The finished gel was clear and stable through several freeze/thaw cycles.

Example 3

A sample of zinc oxide suspension in gelled octyl methoxycinnamate was prepared by using 50.00 wt. % of zinc oxide and 50.00 wt. % of the gelled octyl methoxycinnamate illustrated in Example 2. The finished suspension had good consistency and maintained stability without separation for 15 days under thermal stress.

Example 4

A sample of gelled propylene glycol dicaprylate/caprate (trade name: Estol 1526) was prepared (87.58 wt. % propylene glycol dicaprylate/caprate+12.00 wt. % Kraton G 1780+ 0.40 wt. % Kraton G 1650). The gel was clear at ambient temperature.

Example 5

A sample of gelled isostearyl neopentanoate (trade name: Dermol 185) was prepared (85.58 wt. % isostearyl neopentanoate+14.00 wt. % Septon 1001+0.40 wt. % Kraton G 1650). The finished gel was clear and stable without syneresis.

Example 6

Jojoba oil gel was prepared (91.28% jojoba oil+0.4% Kraton G 1650+8.3% Kraton G 1702). The gel was clear and viscous.

Example 7

Eicosyl erucate (trade name: Erucical EG-20) gel was prepared (91.28% Erucical EG-20+0.4% Kraton G 1650+8.3% Kraton G 1702). The gel was clear and stable without syneresis.

In addition to the above examples of gel compositions, various other gel compositions also were obtained. Tables 3-6 summarize the gel compositions obtained in accordance with embodiments of the invention.

TABLE 3

| INCI Name | Ester (wt. %) | Kraton ® G1650 | Kraton ® G1702 | Kraton ® G1701 | Kraton ® G1780 | Septon ® G1001 | Kraton ® FG1901 | Kraton ® G1652 |
|---|---|---|---|---|---|---|---|---|
| Isopropyl Myristate | 85.28 | 0.4 | 14.3 | | | | | |
|  | 90.58 | 0.4 | 9.00 | | | | | |
| Isopropyl Palmitate | 87.58 | 0.4 | 12.00 | | | | | |
|  | 89.58 | 0.4 | 10.00 | | | | | |
|  | 85.58 | 0.4 | 14.00 | | | | | |
| C12-15 Alkyl Benzoate | 83.58 | 0.4 | 16.00 | | | | | |
|  | 87.58 | 0.4 | 12.00 | | | | | |
|  | 87.98 | | 12.00 | | | | | |
|  | 89.58 | 0.4 | 10.00 | | | | | |
|  | 89.98 | 10.00 | | | | | | |
| Octyl Methoxycinnamate | 89.58 | 0.40 | 10.00 | | | | | |
|  | 83.58 | 0.40 | 16.00 | | | | | |
|  | 85.58 | 0.40 | 14.00 | | | | | |
|  | 81.58 | 0.40 | 12.00 | | | | | |
|  | 83.58 | 0.40 | | 16.00 | | | | |
|  | 87.58 | 0.40 | | 12.00 | | | | |
|  | 85.58 | 0.40 | | 14.00 | | | | |
|  | 89.58 | 0.40 | | 10.00 | | | | |
| Octyl Dodecyl Neopentanoate | 81.98 | | | 12.00 | | | | |
| Isostearyl Neopentanoate | 85.58 | 0.40 | | | | 14.00 | | |
|  | 81.98 | | | 12.00 | | | | |
| Tridecyl Salicylate | 87.58 | 0.40 | 12.00 | | | | | |
|  | 91.28 | 0.4 | 8.30 | | | | | |
| Octyl Dodecanol | 89.58 | 0.4 | | 10.00 | | | | |
|  | 88.89 | | | 6.67 | | | 4.44 | |
|  | 90.00 | | 5.48 | | | | 4.5 | |
|  | 90.00 | | 5.45 | | | | | 4.5 |
|  | 87.58 | 0.4 | 12.00 | | | | | |
|  | 89.58 | 0.4 | 10.00 | | | | | |
| Propylene Glycol Dicaprylate/caprate | 87.58 | 0.4 | | | 12.00 | | | |
| Jojoba Oil | 91.28 | 0.4 | 8.30 | | | | | |

TABLE 4

|  | Polymer Type | Ester (%) | Polymer (%) | Antioxidant (%) |
|---|---|---|---|---|
| 1,2-benzene-dicarboxylic acid, di-C8-10 br alkyl ester | Vector ® 6030 | 91.98 | 8 | 0.02 |
|  | Vector ® 8550 | 91.98 | 8 | 0.02 |
|  | Vector ® 2518P | 91.98 | 8 | 0.02 |
|  | Solprene ® S200 | 91.98 | 8 | 0.02 |
| 1,2-benzene-dicarboxylic acid, di-undecyl ester | Vector ® 6030 | 91.98 | 8 | 0.02 |

TABLE 5

| Oil Type | Polymer Type | Oil (%) | Polymer (%) | Antioxidant (%) |
|---|---|---|---|---|
| Sunflower Seed Oil | Kraton ® D1102 | 91.9 | 8 | 0.10 |
|  | Kraton ® D1133 | 91.9 | 8 | 0.10 |
|  | Kraton ® D 1101 | 91.9 | 8 | 0.10 |
|  | Vector ® 6030 | 91.9 | 8 | 0.10 |
| Corn Oil | Vector ® 6030 | 91.9 | 8 | 0.10 |
| Sesame Oil | Vector ® 6030 | 91.9 | 8 | 0.10 |
| Soybean Oil | Kraton ® D1101 | 89.90 | 10 | 0.10 |
|  | Kraton ® D1102 | 85.98 | 14 | 0.02 |
|  | Vector ® 6030 | 91.90 | 8 | 0.10 |
| Linseed Oil | Kraton ® D1102 | 85.90 | 14 | 0.10 |
|  | Vector ® 6030 | 91.90 | 8 | 0.10 |

TABLE 6

| Oil Type | Oil (%) | Isopropyl Palmitate (%) | Alkyle Galacto-mannon (%) | Antioxidant (%) |
|---|---|---|---|---|
| Sunflower Seed Oil | 46.99 | 46.99 | 6.0 | 0.02 |
|  | 44.99 | 44.99 | 10.0 | 0.02 |
|  | 75.18 | 18.8 | 6.0 | 0.02 |
|  | 71.95 | 18.0 | 10.0 | 0.05 |
| Corn Oil | 75.1 | 18.8 | 6.0 | 0.10 |
|  | 71.9 | 18.0 | 10.0 | 0.10 |
| Soybean Oil | 75.1 | 18.8 | 6.0 | 0.10 |
|  | 71.9 | 18.0 | 10.0 | 0.10 |
| Sesame Oil | 68.9 | 25.0 | 6.0 | 0.10 |
|  | 65.31 | 25.5 | 9.1 | 0.09 |
| Olive Oil | 68.9 | 25.0 | 6.0 | 0.10 |
|  | 65.9 | 25.0 | 9.0 | 0.10 |

Example 8

An in-vivo test was conducted to evaluate the waterproof efficacy of a sunscreen lotion based on a gelled ester composition. The in-vivo test procedure was conducted in accordance with the FDA monographs for sunscreen testing published in Federal Register, Vol. 43, No. 166, Aug. 25, 1978. Briefly, a finished sunscreen lotion was applied to a skin surface which was subsequently submerged in water. Before water immersion, the sun protection factor ("SPF") was measured. After eighty minutes of water immersion, the SPF value was measured again. The percentage of the remaining SPF is indicative of the waterproof efficacy of the sunscreen lotion.

In this example, two sunscreen lotions were prepared according to Table 7. Both lotions contained approximately the same amount of a sunscreen active ingredient, i.e., octyl methoxycinnamate ("OMC"). Sunscreen Lotion A included gelled OMC, whereas Sunscreen Lotion B included neat OMC. Both sunscreen lotions contained approximately the same amounts of other ingredients as indicated in Table 7.

TABLE 7

| Ingredient | Sunscreen Lotion A | Sunscreen Lotion B |
|---|---|---|
| De-ionized water | 45.74 | 45.74 |
| Tetra sodium EDTA | 0.10 | 0.10 |
| Proplyene Glycol | 2.50 | 2.50 |
| Carbopol 940 (2% solution) | 25.00 | 25.00 |
| DEA-cetyl phosphate | 1.00 | 1.00 |
| Cetearyl Alcohol and Ceteareth 20 | 1.50 | 1.50 |
| Mineral Oil | — | 1.26 |
| Octyl Methoxycinnamate | — | 7.50 |
| Octyl Methoxycinnamate + Hydrogenated Ethylene/propylene/styrene copolymers + Hydrogenated Butylene/ethylene/styrene copolymers | 8.76 | — |
| Dimthicone | 2.00 | 2.00 |
| Diisodecyl Adipate | 7.00 | 7.00 |
| $C_{12-13}$ Alkyl Benzoate | 5.00 | 5.00 |
| Triethanol amine | 0.40 | 0.40 |
| Diazolidinyl urea + propylene glycol + Methylparaben + propylparaben | 1.00 | 1.00 |
| Remaining SPF after 80 min water immersion | 84% | 69% |

After eighty minutes of water immersion, the remaining SPF for Sunscreen Lotion A was about 84% of the pre-immersion SPF. As to Sunscreen Lotion B, the remaining SPF was about 69% of its pre-immersion SPF. Therefore, the test result indicates that inclusion of a gelled sunscreen active ingredient increases the waterproof efficacy of the sunscreen lotion.

Example 9

This example shows that gelled esters are comparable to petrolatum as an occlusive agent. An in-vivo skin barrier test was utilized to evaluate a gelled ester's ability to enhance the barrier function of the stratum corneum of human skin. Three different ester gels were formulated and evaluated in this test. Their respective formulations are listed in Table 8.

TABLE 8

| Sample | Intermediate | Ester (wt. %) | Kraton G1701 (wt. %) | Kraton G1650 (wt. %) | Kraton G1701 (wt. %) | Antioxidant (%) |
|---|---|---|---|---|---|---|
| Gel No. 1 | $C_{12-15}$ Alkyl Benzoate | 85.58 | 14.00 | 0.40 | — | 0.02 |
| Gel No. 2 | Isoprpyl Palmitate | 87.58 | 12.00 | 0.40 | — | 0.02 |
| Gel No 3 | Octyl Methoxycinnamate | 85.58 | — | 0.40 | 14.00 | 0.02 |

An independent laboratory conducted Trans-Epidermal Water Loss ("TEWL") testing using the above gel compositions. Thirteen subjects were employed. TEWL measurements were taken on each subject at baseline and at 1, 2, and 3 hours after the application of a test material. A Servomed RTM Evaporimeter was used to measure the effectiveness of a topically applied test material. The evaporimeter samples relative humidity at two points above the skin surface which allowed the rate of water loss to be calculated from the measured humidity gradient. Petrolatum also was included in the measurements. The data obtained from the TEWL measurements are presented in Table

TABLE 9

| Test Material | Baseline | Hour 1 | | Hour 2 | | Hour 3 | |
|---|---|---|---|---|---|---|---|
| | | mean | Δ % | mean | Δ % | mean | Δ % |
| Gel No. 1 | 7.07 | 5.47 | 22.6% | 5.44 | 23.1% | 5.26 | 25.6% |
| Gel No. 2 | 6.66 | 5.37 | 19.4% | 5.14 | 22.8% | 4.72 | 29.1% |
| Gel No 3 | 6.76 | 5.79 | 14.5% | 5.49 | 18.8% | 5.25 | 22.3% |
| Petrolatum | 6.64 | 4.64 | 30.1% | 4.28 | 35.5% | 4.13 | 37.8% |

Note
Δ% = (Baseline − Mean) * 100/Baseline

The data indicate that all three gelled esters are effective in retaining moisture in the skin. Consequently, gelled esters can be used as an occlusive agent in various health and beauty aid compositions.

Example 10

This example shows that a gelled composition has significantly higher loading capacity as a suspension system. To compare the loading capacity of gelled soybean oil with that of neat soybean oil, two experiments were conducted: about 3 grams coated $TiO_2$ powder were suspended in about 97 grams of neat soybean oil; and about 50 grams of the same coated $TiO_2$ powder were suspended in 50 grams of gelled soybean oil. No dispersant agent was used in either suspension system. The gelled soybean oil was made from the following formulation: about 85.9 wt. % of commercially available soybean oil and about 14 wt. % of Kraton RTM D1102. It was observed that only about 2 wt. % of $TiO_2$ remained suspended in the neat soybean oil. In contrast, about 50 wt. % of $TiO_2$ was suspended in the gelled soybean oil. It is surprising that the loading capacity of gelled soybean oil is about 25 times more than that of neat soybean oil. The increased loading capacity by using a gelled naturally-occurring fat or oil should result in improved performance and cost savings.

Accordingly, the gel compositions in accordance with embodiments of the invention have numerous cosmetic and industrial applications. The gel compositions may be used alone or in combination with one or more additional ingredients. For example, the gel compositions are suitable as lubricants, suspending agents, emulsion stabilizers, thickening agents, personal care ingredients, air freshener components, pesticide and insecticide components, ingredients for candle and ornamental products, pharmaceutical carriers and carrier ingredients, ointment base ingredients, sporting goods, and vehicles for carrying other materials. Since esters are generally considered as biodegradable materials, this allows gelled esters to find application in products where minimal pollution is desired. Examples include fishing line lubricant, solder flux, agricultural dust reduction and lubrication, textile coating, protective coating for transporting fragile or environmentally-sensitive materials, and biodegradable oils and greases.

It has been discovered that the gel compositions in accordance with embodiments of the invention keep solids and/or liquids substantially uniformly suspended and evenly dispersed over a substantial period of time. The suspended liquids and/or solids may be present in the gel in amounts of up to about 95 weight percent. Suitable solids and/or liquids that can be suspended in the gel include any solid or non-hydrocarbon oil liquid which will disperse into the gel and remain substantially suspended or evenly dispersed therein.

Examples of suitable solids include, but are not limited to, zinc oxide, coated zinc oxide, surface-treated zinc oxide, titanium dioxide, coated titanium dioxide, surface-treated titanium dioxide, phosphorescent substances, fluorescent materials, molybdenum oxide, zinc sulfide, copper-dopped zinc sulfide, graphite, explosive materials, pesticides, herbicides, fungicides, insecticides, plasticizers, air sensitive chemicals, moisture sensitive chemicals, boron nitride, iron oxides, talc, mica, plastics, polymers, silica, silicon dioxide, aluminum oxide, inorganic materials, organometallic materials, metal particles, medical materials (such as antibacterials, antibiotics, antimicrobials, antifungals, and anesthetics), glass, clays, gums, capsules containing an active ingredient, starch, modified starch, other encapsulated materials, and mixtures thereof.

Examples of oil insoluble liquids which can be suspended in the gels include, but are not limited to, water, water containing one or more water soluble materials, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and the mixtures thereof.

Pending U.S. patent application Ser. No. 09/007,838, entitled "Hydrocarbon Gels as Suspending and the Dispersing Agents and Products," filed Jan. 15, 1998, discloses methods of making a suspension system based on gelled hydrocarbons. The disclosed methods can be utilized in embodiments of the invention to make suspension systems which are based on gelled esters, gelled alcohols, gelled naturally-occurring fats and oils, or gelled ethers. The disclosure of the above-referenced patent application is incorporated by reference in its entirety herein.

The gel compositions in accordance with embodiments of the invention also have a wide spectrum of cosmetic applications when the gel compositions include an effective amount of one or more cosmetic and health and beauty aid ingredients. By "effective amount," it is meant that a sufficient amount of the ingredient is present to be effective for the indicated purpose in the composition. An effective amount may range from about 0.001 to about 80 wt. %. By "cosmetic and health and beauty aid ingredients," it is meant any material which can be applied topically to the human skin or any part thereof for cleansing, beautifying, promoting attractiveness, and protecting or altering the appearance of the skin without altering or interfering with the physiological competence of the human skin or body. Included within this definition are creams, lotions, emollients, fragrance oils, moisturizers, humectants, cosmetic oils, and so on. The gel compositions in accordance with embodiments of the invention also may contain skin care preservatives, diluents, surfactants, anti-wrinkle agents, and the like.

Furthermore, the gel compositions may be utilized to manufacture various over-the-counter ("OTC") products. An OTC product may be made entirely from a gel composition; or only a component of the OTC is made from the gel composition. Examples of OTC products include, but are not limited to, antiperspirants, lip balms, and sunscreen (e.g., natural sunblocks, such as submicron particles of metal oxides or synthetic sunblock agents, such as octyl methoxycinnamate and benzophenone-3).

As mentioned above, the gel composition in accordance with embodiments of the invention may be utilized as carrier vehicles for topical administration of various cosmetic and health and beauty aid materials to the skin. Thus, such materials can be incorporated into the gel which are applied to the skin to be absorbed, to form a film on the skin, to provide a cooling sensation, to treat dry skin or oily skin, to work a material into the skin, to alter the overall texture of the skin, or to change color. All of these effects are sought to be achieved by various health and beauty aid products. Methods for making such skin care products are known in the art. For example, U.S. Pat. No. 5,558,872 discloses a clear gelled mineral oil based skin protectant. Similar skin protectants may be made by substituting the mineral oil gel by the gel compositions in accordance with embodiments of the invention. The disclosure of U.S. Pat. No. 5,558,872 is incorporated by reference in its entirety herein.

It is noted that preferred uses of the gel compositions in accordance with embodiments of the invention include formation of thickened liquids, soft gels and semi-solid gels. Gels are particularly useful in waterproofing sunscreen compositions, makeup, mascara, etc. They also are useful in petrolatum-based products, such as petroleum jelly, makeup foundation, and night creams. They also can be used as substitutes for water-soluble polymers in products, such as lip rouge-cream, eyeliner liquid, and the like. They also may be used as a gelling agent in facial oil.

Semi-solid or solid gels have applications as toiletry sticks, such as a stick insect repellant or a matrix for clear or opaque stick products, which include deodorants, antiperspirants, lipsticks, analgesics, blushers, solid lotions and solid absorbable flexible gels. Methods for making such cosmetic sticks are known. For example, U.S. Pat. No. 5,756,082 discloses a cosmetic stick composition based on a hydrocarbon oil gel. The disclosed hydrocarbon oil gels may be substituted by the gel compositions in accordance with embodiments of the invention to make cosmetic stick compositions. The disclosure of U.S. Pat. No. 5,756,082 is incorporated by reference in its entirety herein.

As demonstrated above, the gel compositions in accordance with embodiments of the invention have a wide range of industrial and cosmetic applications. When so used, the gel compositions may exhibit one or more of the following properties or advantages: transparency; compatibility with active ingredients; reduction or elimination of syneresis; ability to act as a vehicle to provide a stable suspension of an ingredient; moisturization; enhancement of wash-off resistance; provision of improved SPF when formulated into sunscreen products; reduction in absorption and irritation; elimination or minimization of whitening effect; ability to act as a cosmetic base; controlled release of volatile ingredients; and formulation with less emulsifiers. Other properties and advantages are apparent to a person of ordinary skill in the art.

While the invention has been described with respect to a limited number of embodiments, modifications and variations therefrom exist. For example, although suitable esters, ethers, alcohols, and naturally-occurring fats and oils have been described with some depth, other compounds also can be used. Additional suitable esters may include alkoxylated fatty acids, glyceryl ethers, and sorbitan derivatives. Additional suitable alcohols may include alkanolamides, alkanolamines, fatty alcohols, polyols, phenols, and sterols. Additional suitable ethers include heterocyclic ethers, e.g., tocopherol, alkoxylated alcohols, alkoxylated amides, alkoxylated amines, alkoxylated carboxylic acids, polymeric ethers, and glyceryl ethers. Similarly, naturally-occurring fats and oils may include so-called "essential oils," which are volatile organic constituents of plants normally obtained by distillation. In addition to the above-described compounds, aldehydes and ketones also may be formed into gel compositions in accordance with embodiments of the invention. The appended claims are intended to encompass all such modifications and the variations as falling within the scope of the invention.

What is claimed is:

1. A gel composition, comprising:
an ester compound;
a diblock copolymer comprising at least one rigid block selected from the group consisting of polystyrene, polyethylene, polyvinylchloride, and phenolics, and one elastic block selected from the group consisting of ethylene/butadiene copolymers, polyisoprene, polybutadiene, ethylene/propylene copolymers, and ethylene-propylene/diene copolymers, wherein the diblock polymer has a polystyrene content between about 28% and about 40%; and
one or more polymers selected from the group consisting of a triblock copolymer, a star polymer, a radial polymer, a multi-block copolymer, and combinations thereof, wherein the triblock copolymer, star polymer, radial polymer, and multi-block copolymer have a polystyrene content between about 7% and about 30%;
wherein the gel composition is substantially free of mineral oils,
wherein the ester is represented by one of the following formulas:

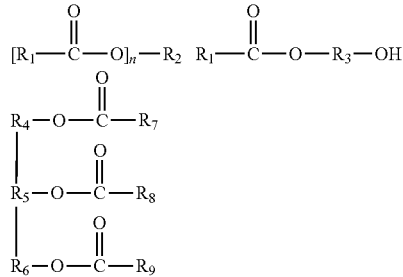

wherein n=1, 2, 3, or 4, and
$R_1$ is hydrogen, hydrocarbyl, phenyl, methoxyphenyl, alkylphenyl, substituted alkyl, or substituted phenyl, $R_2$ is hydrogen, hydrocarbyl, phenyl, methoxyphenyl, alkylphenyl, substituted alkyl, substituted phenyl, alkylene, phenylene, substituted alkylene, or substituted phenylene, and $R_3$ is alkylene, phenylene, substituted alkylene, or substituted phenylene, and
wherein $R_4$, $R_5$ and $R_6$ individually are alkylene, phenylene, substituted alkylene, or substituted phenylene, $R_7$, $R_8$ and $R_9$ individually are hydrogen, hydrocarbyl, phenyl, methoxyphenyl, alkylphenyl, substituted alkyl, or substituted phenyl,
and wherein the diblock copolymer is present in the amount of about 5% to about 20% by weight of the gel, the one or more polymers is present in the amount of about 0.1% to about 5% by weight of the gel, and the ester compound is present in the amount of about 80% to about 92% by weight of the gel.

2. The gel composition of claim 1, wherein the ester is selected from the group consisting of isopropyl myristate, isopropyl palmitate, $C_{12}$ to $C_{15}$ alkyl benzoate, octyl methoxycinnamate, octyl dodecyl neopentanoate, propylene glycol dicaprylate/caprate, jojoba oil, and isostearyl neopentanoate.

3. The gel composition of claim 1, wherein the diblock copolymer is selected from the group consisting of styrene-ethylene/propylene copolymers, styrene-ethylene/butadiene copolymers, styrene-isoprene copolymers, and styrene-butadiene copolymers.

4. The gel composition of claim 1, wherein the one or more polymers is a triblock copolymer selected from the group consisting of styrene-ethylene/propylene-styrene copolymers, styrene-ethylene/butadiene-styrene copolymers, styrene-isoprene-styrene copolymers, and styrene-butadiene-styrene copolymers.

5. The gel composition of claim 1, wherein the diblock copolymer is hydrogenated.

6. The gel composition of claim 1, wherein the one or more polymers is a hydrogenated triblock copolymer.

7. The gel composition of claim 1, wherein the triblock copolymer includes a grafted functional group.

8. The gel composition of claim 1, further comprising a suspended component.

9. The gel composition of claim 8, wherein the suspended component is a solid selected from the group consisting of organic materials, inorganic materials, organometallic materials, phosphorescent materials, and fluorescent materials.

10. The gel composition of claim 8, wherein the suspended component is a solid selected from the group consisting of zinc oxide, coated zinc oxide, surface-treated zinc oxide, titanium dioxide, surface-treated titanium dioxide, graphite, explosives, air-sensitive chemicals, moisture-sensitive chemicals, boron nitride, iron oxides, talc, mica, plastics, polymers, silica, silicon dioxide, aluminum oxide, metal particles, antibacterials, antibiotics, anesthetics, glass, clays, gums, capsules containing an active ingredient, starch, modified starch, other encapsulated materials, and combinations thereof.

11. The gel composition of claim 8, wherein the suspended component is a liquid selected from the group consisting of water, water containing a water-soluble material, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and combinations thereof.

12. The gel composition of claim 1, further comprising an active ingredient.

13. The gel composition of claim 12, wherein the active ingredient is selected from the group consisting of sunscreens, antiperspirants, deodorants, perfumes, cosmetics, emollients, insect repellants, pesticides, herbicides, fungicides, plasticizers, insecticides, and medicaments.

14. A method of making a gel composition, comprising:
mixing an ester compound with a diblock copolymer compound having at least one rigid block selected from the group consisting of polystyrene, polyethylene, polyvinylchloride, and phenolics, and one elastic block selected from the group consisting of ethylene/butadiene copolymers, polyisoprene, polybutadiene, ethylene/propylene copolymers, and ethylenepropylene/diene copolymers, wherein the diblock polymer has a polystyrene content between about 28% to about 40%, and one or more polymers selected from the group consisting of a triblock copolymer, a star polymer, a radial polymer, a multi-block copolymer, and combinations thereof, wherein the triblock copolymer, star polymer, radial polymer, and multi-block copolymer have a polystyrene content between about 7% and about 30%;
heating the mixture;
agitating the mixture until the mixture becomes homogeneous; and
cooling the mixture,
wherein the gel composition is substantially free of mineral oils, wherein the ester is represented by one of the following formulas:

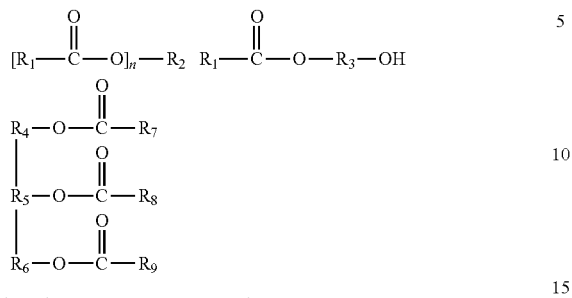

wherein n=1, 2, 3, or 4, and $R_1$ is hydrogen, hydrocarbyl, phenyl, methoxyphenyl, alkylphenyl, substituted alkyl, or substituted phenyl, $R_2$ is hydrogen, hydrocarbyl, phenyl, methoxyphenyl, alkylphenyl, substituted alkyl, substituted phenyl, alkylene, phenylene, substituted alkylene, or substituted phenylene, $R_3$ is alkylene, phenylene, substituted alkylene, or substituted phenylene, $R_4$, $R_5$ and $R_6$ individually are alkylene, phenylene, substituted alkylene, or substituted phenylene, $R_7$, $R_8$ and $R_9$ individually are hydrogen, hydrocarbyl, phenyl, methoxyphenyl, alkylphenyl, substituted alkyl, or substituted phenyl, and wherein the polymer compound is present in the amount of about 5% to about 20% by weight of the gel and the ester compound is present in the amount of about 80% to about 92% by weight of the gel.

* * * * *